United States Patent
Häll et al.

(10) Patent No.: US 9,984,457 B2
(45) Date of Patent: May 29, 2018

(54) AUTOMATED GROSSING IMAGE SYNCHRONIZATION AND RELATED VIEWERS AND WORKSTATIONS

(71) Applicant: Sectra AB, Linköping (SE)

(72) Inventors: Fredrik Häll, Linköping (SE); Kristian Köpsén, Linköping (SE); Jesper Molin, Linköping (SE); Joackim Pennerup, Linköping (SE); Olle Westman, Linköping (SE); Tobias Dahlberg, Linköping (SE); Claes Lundström, Linköping (SE)

(73) Assignee: Sectra AB, Linkoping (SE)

( * ) Notice: Subject to any disclaimer, the term of this patent is extended or adjusted under 35 U.S.C. 154(b) by 191 days.

(21) Appl. No.: 14/659,229

(22) Filed: Mar. 16, 2015

(65) Prior Publication Data

US 2015/0279026 A1    Oct. 1, 2015

Related U.S. Application Data

(60) Provisional application No. 61/970,608, filed on Mar. 26, 2014.

(51) Int. Cl.
| | |
|---|---|
| *G06K 9/00* | (2006.01) |
| *G06T 7/00* | (2017.01) |
| *G06F 19/00* | (2018.01) |

(Continued)

(52) U.S. Cl.
CPC .......... *G06T 7/0012* (2013.01); *G06F 19/321* (2013.01); *G06K 9/00* (2013.01);
(Continued)

(58) Field of Classification Search
CPC ......... G06T 7/0012; G06T 2207/10056; G06T 2207/30024; G06T 2200/24; G06T 7/0024;
(Continued)

(56) References Cited

U.S. PATENT DOCUMENTS

| | | |
|---|---|---|
| 6,044,165 A | 3/2000 | Perona et al. |
| 6,721,001 B1 | 4/2004 | Berstis |

(Continued)

FOREIGN PATENT DOCUMENTS

WO    WO 2010/027430 A2    3/2010

OTHER PUBLICATIONS

Bell et al., The Efficient Operation of the Surgical Pathology Gross Room, Biotech Histochem, 2008, pp. 71-82, vol. 83, No. 2.
(Continued)

*Primary Examiner* — Vu Le
*Assistant Examiner* — Guillermo Rivera-Martinez
(74) *Attorney, Agent, or Firm* — Myers Bigel, P.A.

(57) ABSTRACT

Methods, systems, workstations, viewers, grossing stations and computer include a display and a viewer circuit configured to cause the display to concurrently display: (i) a macroscopic view of a grossing specimen with virtual cut location marks associated with orientation and location of actual physical cut locations used to obtain tissue samples from the grossing specimen and (ii) at least one digital microscopic whole-slide image (WSI) of a tissue section from the specimen. The display can show the at least one WSI image on the display with a relevant cut location mark on the macroscopic view shown visually enhanced from other cut location marks on the macroscopic view to thereby allow a user to visually connect where the tissue section in the WSI image was obtained during a grossing procedure.

29 Claims, 12 Drawing Sheets
(3 of 12 Drawing Sheet(s) Filed in Color)

(51) Int. Cl.
*G06T 1/00* (2006.01)
*G06T 11/20* (2006.01)

(52) U.S. Cl.
CPC ..... *G06K 9/00127* (2013.01); *G06K 9/00979* (2013.01); *G06T 1/0007* (2013.01); *G06T 7/0014* (2013.01); *G06T 11/203* (2013.01)

(58) Field of Classification Search
CPC .......... G06T 2207/30004; G06K 9/627; G06F 19/366; G06F 3/04845; G06F 3/0484
See application file for complete search history.

(56) References Cited

U.S. PATENT DOCUMENTS

| | | |
|---|---|---|
| 7,571,728 B2 | 8/2009 | Forman et al. |
| 8,388,891 B2 | 3/2013 | Lefebvre |
| 8,501,435 B2 | 8/2013 | Gustafsson |
| 8,645,167 B2 | 2/2014 | Chirica et al. |
| 9,412,162 B2 | 8/2016 | Molin et al. |
| 2004/0085443 A1 | 5/2004 | Kallioniemi |
| 2005/0159759 A1 | 7/2005 | Harbaugh et al. |
| 2005/0245808 A1 | 11/2005 | Carson |
| 2006/0159325 A1 | 7/2006 | Zeineh et al. |
| 2006/0236703 A1* | 10/2006 | Rada ................. A01N 1/02 62/62 |
| 2007/0118139 A1 | 5/2007 | Cuellar et al. |
| 2007/0206105 A1* | 9/2007 | Cooke ................. G02B 21/367 348/294 |
| 2007/0269085 A1* | 11/2007 | Oshiro ................. G02B 21/365 382/128 |
| 2008/0123910 A1* | 5/2008 | Zhu ................. A61B 90/36 382/128 |
| 2010/0093023 A1* | 4/2010 | Gustafsson ............ G01N 1/286 435/40.52 |
| 2010/0210939 A1* | 8/2010 | Hartmann ............... A61B 5/062 600/424 |
| 2010/0260407 A1* | 10/2010 | Eichhorn ............... G02B 21/26 382/133 |
| 2011/0040169 A1* | 2/2011 | Kamen ................. A61B 6/037 600/411 |
| 2011/0060766 A1* | 3/2011 | Ehlke ................. G06F 3/0481 707/802 |
| 2012/0072452 A1* | 3/2012 | Stratman ................ G06Q 10/06 707/772 |
| 2012/0320094 A1* | 12/2012 | Ruddle ................ G02B 21/367 345/660 |
| 2013/0188857 A1 | 7/2013 | Yoshihara |
| 2015/0117730 A1* | 4/2015 | Takayama ................ G06K 9/46 382/128 |
| 2015/0279032 A1 | 10/2015 | Hall |
| 2016/0019695 A1* | 1/2016 | Chukka ................. G06T 7/0014 382/128 |

OTHER PUBLICATIONS

Kain et al., The Chick Embryo as an Expanding Experimental Model for Cancer and Cardiovascular Research, Developmental Dynamics, Dec. 19, 2013, pp. 216-228, vol. 243.

European Search Report for related EP application No. EP15160731.4, dated Sep. 16, 2015, 11 pages.

European Search Report for related EP application No. EP15160730.6, dated Sep. 16, 2015, 13 pages.

MicroPath D, Digital Imaging System for Grossing, CMI, Blog Archive, Dec. 20, 2013, http://web.archive.org/web/20131220165540/http://choicemedind.com/macropath-d-digital-imaging-system-for-grossing/, printed from the internet Aug. 24, 2015, 4 pages.

Amin et al. "Integration of digital gross pathology images for enterprise-wide access", *J Pathol Inform*, Mar. 16, 2012, vol. 3 Issue 10.

Bowen et al. "New region feature descriptor-based image registration method", 2012 IEEE International Conference on Systems, Man, and Cybernetics (SMC), pp. 2489, 2494, Oct. 14-17, 2012.

Cooper L. et al. "Digital Pathology: Data-Intensive Frontier in Medical Imaging", *Proceedings of the IEEE*, vol. 100, No. 4, Apr. 2012, pp. 991-1003.

USPTO Non-Final Office Action for related U.S. Appl. No. 14/659,236, dated Jun. 15, 2016, 20 pages.

'MacroStation' Brochure *3DHistech* (3 pages) (Nov. 21, 2013).

Tucker, F. Lee "Imaging-Assisted Large-Format Breast Pathology: Program Rationale and Development in a Nonprofit Health System in the United States" *International Journal of Breast Cancer* 2012:1-16 (2012).

Yagi, Yukako "Challenges in Whole Slide Image Based 3D Imaging" *Assistant Professor of Pathology, Harvard Medical School* (69 pages) (2013).

Laurinaviciene et al. "Digital immunohistochemistry platform for the staining variation monitoring based on integration of image and statistical analyses with laboratory information system" *Diagnostic Pathology* 9(Suppl 1):S10 (2014).

Laurinavicius et al. "Digital immunohistochemistry: new horizons and practical solutions in breast cancer pathology" *Diagnostic Pathology* 8(Suppl 1):S15 (2013).

Polley et al. "An International Ki67 Reproducibility Study" *Journal of the National Cancer Institute* 105:1897-1906 (2013).

Pretorius et al. "Visualization of Parameter Space for Image Analysis" *IEEE Transactions on Visualization and Computer Graphics* 17(12):2402-2411 (2011).

Rojo et al. "Critical Comparison of 31 Commercially Available Digital Slide Systems in Pathology" *International Journal of Surgical Pathology* 14(4):285-305 (2006).

* cited by examiner

AUTOMATED GROSSING IMAGE SYNCHRONIZATION AND RELATED VIEWERS AND WORKSTATIONS

RELATED APPLICATIONS

This application claims the benefit of and priority to U.S. Provisional Application Ser. No. 61/970,608, filed Mar. 26, 2014, the contents of which are hereby incorporated by reference as if recited in full herein.

FIELD OF THE INVENTION

The present invention is related to medical microscopy imaging within the digital pathology domain.

BACKGROUND

In the histopathology workflow, tissue samples can be cut or otherwise excised from a gross specimen, a procedure known as "grossing". These (sub)samples then go through a number of processing steps in the laboratory, typically ending up as stained tissue sections mounted on glass slides. In a digital pathology workflow, these glass slides are then scanned into digital histology microscopy images. While the pathologist (a specialist physician) performs the microscopic image review, the grossing is frequently done by other staff, such as technicians, resident physicians or other pathologists. For an overview of grossing procedures, see Theory and Practice of Histological Techniques, John D. Bancroft, Elsevier Health Sciences, the content of which are hereby included by reference as if recited in full herein.

In histopathology, the connection between a respective gross (or "grossing") specimen and corresponding histology slides can be of vital importance. A macroscopic examination is done for most specimens and diagnostic findings are documented. In order to relate to these findings during microscopic review, the location of the findings relative to a respective tissue specimen are often marked with colored dye during the grossing procedure. The dye is preserved in the tissue samples through the subsequent processing and shows up in the microscopic images of the tissue sections on the glass slides. The location of the cut in the specimen is also of high importance. Knowing both the macroscopic orientation and the location of the tissue section relative to the tissue specimen are particularly important when assessing margins. For example, if cancerous cells are found in a region close to a resection border, the risk is high that there are remaining cancerous cells in the patient. Thus, the relation between macroscopic and microscopic findings is important and often affects therapy and medical decisions such as therapeutic treatment selections for the patient.

To meet the informational need, the pathologist performing the microscopic review should be provided a description of the gross specimen. In the past, such information was in the form of a manually drawn sketch on paper or in the form of a digital photograph(s) of the specimen from a macroscopic camera. If there is such a macroscopic camera, it may operate with software that allows manual drawing of cuts and other annotations such as measurements on the gross image.

Unfortunately, manually entered physical or digital markings on the macroscopic images can be relatively cumbersome to make, especially in the wet and dirty environment of a grossing station, and they can be imprecise or subjective due to the manual nature of the marking. Furthermore, at the microscopic review, the pathologist is required to cognitively make the connections between the markings and the scanned slides and regions of the slides.

SUMMARY

Embodiments of the invention provide improved grossing systems, viewers and workstations that can provide more intuitive viewer options and/or alternative image processing that can facilitate efficient histology reviews.

Embodiments of the invention provide automated electronic marking on gross images and an image processing method, circuit, viewer, grossing station and system providing image synchronization of slides of tissue sections automatically correlated to a specimen and a physical location on a macroscopic image(s) for histopathology.

A histopathology and/or cytopathology viewer, comprising: a display; and a viewer circuit configured to cause the display to concurrently display: (i) a macroscopic view of a grossing specimen with virtual cut location marks associated with orientation and location of actual physical cut locations used to obtain tissue samples from the grossing specimen and (ii) at least one digital microscopic whole-slide image (WSI) of a tissue section from the specimen. For the at least one WSI image on the display, a relevant cut location mark is shown visually enhanced from other cut location marks on the macroscopic view to thereby allow a user to visually connect where the tissue section in the WSI image was obtained during a grossing procedure.

The viewer circuit can be configured to visually change a display parameter of at least one of: (a) a virtual cut location mark on the macroscopic view that is associated with a location on the specimen from which a tissue section of the at least one WSI in the viewer display was obtained; or (b) virtual cut location marks on the macroscopic view that are not associated with the tissue section of the at least one WSI in the viewer to thereby visually enhance the relevant cut mark location.

The viewer may be configured to provide thumbnail WSI images of slides associated with the grossing specimen of a patient and visually change a display parameter of a thumbnail associated with the at least one WSI in the viewer.

A perimeter of the thumbnail or thumbnails associated with the at least one WSI in the viewer display can be visually enhanced and/or other thumbnails are dimmed or faded in the display window. The virtual cut location marks can be provided as overlay linear objects on the macroscopic view. A virtual cut location mark on the macroscopic view that is associated with a location on the specimen from which a tissue section of the at least one WSI in the viewer display was obtained can be visually highlighted, increased in intensity or changed in color relative to other virtual cut mark locations to thereby visually connect the WSI image in the view to a correct virtual cut location mark.

The viewer circuit can be configured to analyze scanned WSI images for determining color and color location and adjust an orientation of the WSI image for the viewer to consistently provide views of the WSI images to the display in a common orientation with respect to a tissue sample location and orientation in or on the grossing specimen based on the determined color.

Other embodiments are directed to a grossing workstation. The workstation includes: a cut mark location identification circuit; at least one camera over a workspace at the workstation in communication with the cut mark location identification circuit; and a cutting instrument in communication with the cut mark location identification circuit. The cut mark location identification circuit can be configured to identify physical cut mark locations on a grossing specimen and generate corresponding virtual cut location marks on a macroscopic image or model of the specimen for a viewer. A respective virtual cut location mark can correspond to a physical cut location made by the cutting instrument on the grossing specimen used to obtain a tissue sample such that the virtual cut location marks are given a correct spatial position on the macroscopic image or model of the specimen for the viewer.

The cut mark location circuit can analyze a plurality of macroscopic images of the specimen obtained by the at least one camera during a grossing procedure of the specimen, including at least one base macroscopic image obtained prior to a physical cutting to obtain a tissue sample. The cut mark location identification circuit can be configured to electronically place the virtual cut location marks as overlay cut location objects on the macroscopic image or model of the specimen for the viewer.

The cut mark location identification circuit can be configured to electronically track movement of the cutting instrument in the workspace.

The cut mark location identification circuit can be configured to employ image recognition of movement and location of the cutting instrument in images obtained by the at least one camera to generate the virtual cut mark locations on the macroscopic image or model.

The cutting instrument can be configured with a defined leading end portion shape which has a distinct conspicuous visual appearance detectable by image recognition to allow the cut mark location identification circuit to identify movement and contact of the cutting instrument for identifying the placement and orientation of the respective virtual cut location marks.

The cut mark location circuit can be configured to employ a hands-free command or input from a user to initiate identifying a cut location.

Other embodiments are directed to methods of obtaining and/or processing digital pathology and cytology images for viewing. The methods include: electronically identifying when a cutting instrument is approaching and/or on a grossing specimen; and automatically electronically generating virtual cut location marks on a digital macroscopic image or model of a grossing specimen based on the electronic identification, wherein a respective virtual cut location mark corresponds to a physical cut location made by the cutting instrument on the grossing specimen used to obtain a tissue sample such that the virtual cut location is given a correct spatial position on the macroscopic image or model of the specimen.

The method can include electronically automatically obtaining a plurality of macroscopic images of the specimen during a grossing procedure of the specimen, including at least one base macroscopic image obtained prior to one or more physical cutting to obtain a tissue sample, and placing the virtual cut location marks on one or more of the obtained macroscopic images or model of the specimen for display in a viewer.

The electronic identification can be carried out by electronically tracking movement of the cutting instrument.

The electronic identification can be carried out using image recognition of movement and location of the cutting instrument in the obtained images.

The electronic identification of the cutting instrument can be carried out using image recognition of a defined leading end portion configuration which is configured as to have a defined distinct conspicuous visual appearance detectable by image recognition.

The electronic identification can be initiated with a hands-free command to a cut location identification circuit in communication with a grossing workstation.

The electronic identification can be initiated by the cutting instrument transmitting a wireless signal at a time of a cut.

The automatic electronic generation of the virtual cut location marks can include electronically generating an electronic overlay of at least one cut location object provided as a linear mark and displaying the overlay on a macroscopic digital image or model of the specimen.

The method can also include concurrently displaying (i) a macroscopic image of the specimen with the virtual cut location marks with (ii) at least one digital microscopic whole-slide image (WSI) of tissue from the specimen. A virtual cut location mark associated with the at least one digital WSI can be visually enhanced relative to other cut location marks when it is associated with where a tissue section from the WSI was obtained from the specimen.

The virtual cut location marks can be shown as respective overlays on the macroscopic image with the visual enhancement provided by highlighting a virtual cut location mark whenever it corresponds to a microscopic WSI image in a viewer.

The method may include electronically automatically obtaining a plurality of macroscopic images of the specimen during a grossing procedure of the specimen, including at least one base macroscopic image obtained prior to any physical cutting to obtain tissue samples, and placing the virtual cut location marks on one or more of the obtained macroscopic images or a model of the specimen for a viewer macroscopic image; and may also include electronically adjusting for movement of the specimen during a grossing procedure using the base image and one or more of the subsequent plurality of images to register respective virtual cut locations to the viewer macroscopic image or model.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF EMBODIMENTS OF THE INVENTION

Figure 1:
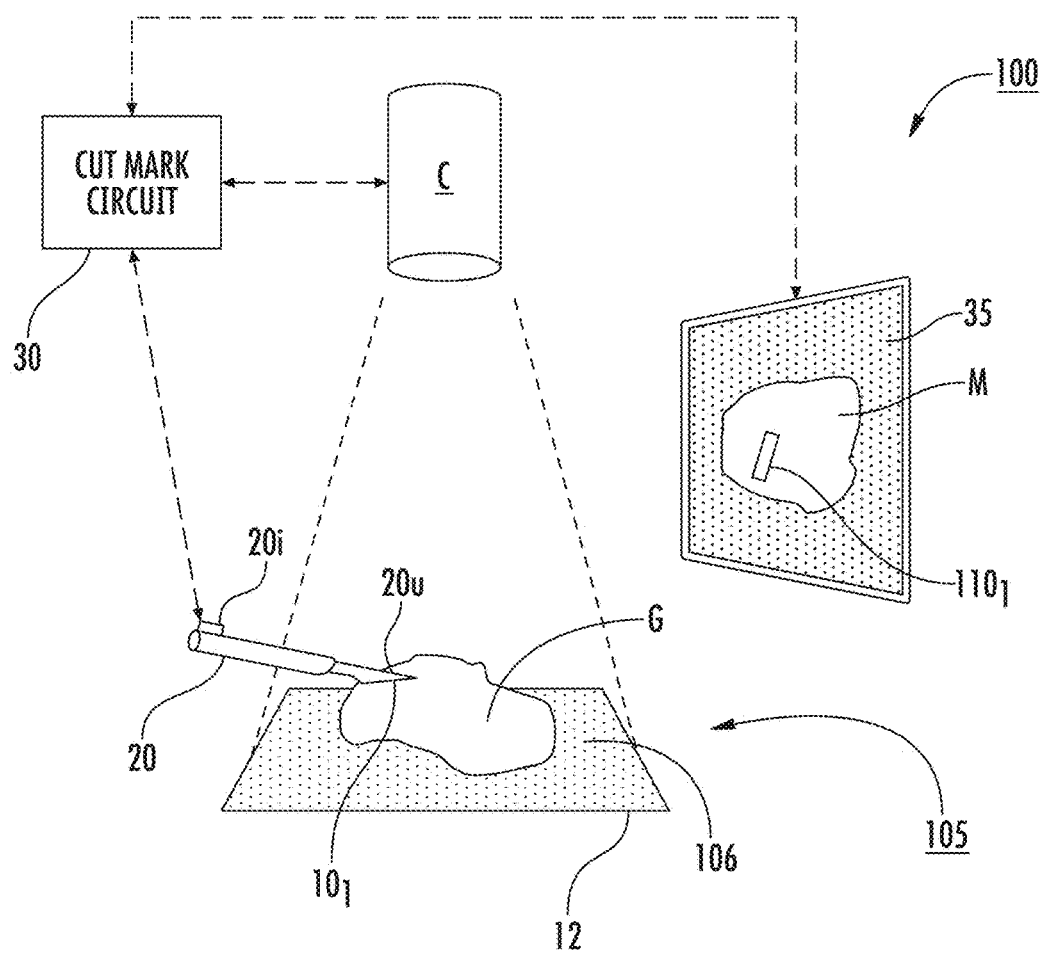
FIG. 1 is schematic illustration of a grossing station accommodating automated visual representations of cut mark locations on a macroscopic image corresponding to cut locations of actual tissue samples from a specimen according to embodiments of the present invention.

The present invention will now be described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit or flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. Like numbers refer to like elements throughout. In the figures, the thickness of certain lines, layers, components, elements or features may be exaggerated for clarity. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. The phrase "in communication with" refers to direct and indirect communication. Although described or shown with respect to one embodiment, the features so described or shown can apply to other embodiments.

The term "circuit" refers to software embodiments or embodiments combining software and hardware aspects, features and/or components, including, for example, at least one processor and software associated therewith embedded therein and/or executable by and/or one or more Application Specific Integrated Circuits (ASICs), for programmatically directing and/or performing certain described actions, operations or method steps. The circuit can reside in one location or multiple locations, it may be integrated into one component or may be distributed, e.g., it may reside entirely in a workstation or single computer, partially in one workstation, cabinet, or computer, or totally in a remote location away from a local display at a workstation. If the latter, a local computer and/or processor can communicate over a LAN, WAN and/or internet to transmit patient macroscopic and microscopic images.

The term "automatically" means that the operation can be substantially, and typically, entirely, carried out without human or manual input, and is typically programmatically directed and/or carried out. The term "electronically" includes both wireless and wired connections between components. The terms "display" and "screen" are used interchangeably.

The term "programmatically" means that the operation or step can be directed and/or carried out by a digital signal processor and/or computer program code. Similarly, the term "electronically" means that the step or operation can be carried out in an automated manner using electronic components rather than manually or using merely mental steps.

The term "clinician" refers to a pathologist, physician, oncologist, or other personnel desiring to review tissue sample data of a subject, which is typically a live human or animal patient but forensic uses are also contemplated.

The term "user" refers to a person or device associated with that person, that uses the described and/or claimed feature or item, such as a technician, pathologist or other expert, or clinician or even a patient.

The term "about" means that the recited parameter can vary from the noted value, typically by +/−20%.

The term "PACS" refers to a PICTURE ARCHIVING AND COMMUNICATION SYSTEM.

The term "magnification" means the image resolution measured in micrometers per pixel, applicable both for the scanned image and the images displayed on screen. Higher magnification corresponds to a lower micrometer per pixel value than lower magnification and vice versa.

The term "high magnification" means displaying an image with an on-screen magnification relatively close to the magnification with which the original image was scanned. Current (2013) clinical scanning protocols commonly employ 200 times or 400 times magnification, corresponding to 0.5 and 0.25 micrometers per pixel respectively. In this case "high magnification" corresponds to magnification range of between about 0.25-1.0 micrometers per pixel.

The term "low magnification" means displaying an image with an on-screen magnification substantially lower than the magnification with which the original image was scanned. In the case of using a scanning protocol of 0.5 or 0.25 micrometers per pixel, "low magnification" corresponds to magnification range of about 2 micrometers per pixel and above, for example 10 micrometers per pixel.

The term "visually enhanced" means that at least one display parameter is adjusted so that one or more noted features are visually dominant relative to other related features, e.g., cut mark locations and/or thumbnail images, for example. The display parameter can comprise brightness, opacity, color, color saturation and the like. Either the display parameter of the visually enhanced feature is adjusted and/or the display parameter of a non-relevant feature is adjusted, e.g., the visually enhanced feature can be shown with increased brightness, intensity or a bolder or more prominent color and/or the non-relevant features can be shown with reduced brightness and/or intensity or in a less prominent color.

The term "model" refers to a rendered representation of the grossing specimen rather than an actual image obtained by a camera.

A grossing workstation refers to a workstation where gross examination or "grossing" is carried out by which pathology "grossing specimens" are inspected, typically with the naked eye, to obtain diagnostic information, while being processed for further microscopic evaluation. There are usually two end products of the gross examination of a surgical specimen. The first is the gross description, a document which serves as the written record of the examiner's findings, and is included in the final pathology report. The second product is a set of tissue blocks, typically postage stamp-sized portions of tissue sealed in plastic cassettes, which will be processed into slides for microscopic examination.

According to the instant application, the grossing workstation can be configured to obtain or capture at least one macroscopic image of a grossing by at least one digital camera. The term "macroscopic image" refers to an image of a the grossing specimen that is to be evaluated and from which discrete tissue samples will be obtained for further processing and digital microscopic WSI of thin tissue sections. The WSI can be described as virtual microscopy for cytopathology.

A "grossing specimen" ("specimen") is a piece of tissue/organ for pathology evaluation, which can be as large as an entire breast or large portion of an intestine. Small pieces of tissue that are obtained (e.g., cut) at grossing can be called "samples" of a specimen. It is also noted that some specimens are so small when they arrive at a pathology evaluation site (such as prostate screening biopsies, which are just a thin thread) that no grossing is necessary. These small specimens typically just proceed to the next step in the laboratory processing. The large specimens (and respective tissue samples) and small specimens can all be referred to as "biopsies." Tissue samples from a specimen or a small specimen itself can be put in one or more paraffin blocks as is well known to those of skill in the art. From a block, micrometer-thin sections (slices) are generated and put onto glass slides for WSI evaluation or virtual microscopy. The present application is particularly useful for specimens requiring grossing "G." Thus, for purposes of the instant application, a "tissue sample" refers to pieces obtained (e.g., cut) from a specimen G during grossing. The slides comprise thin sections of one or more tissue samples from one or more blocks.

During processing both dyes and stains can be used. A dye is applied at grossing to identify an excision or cut site for a particular tissue sample, or, more commonly, the orientation of the sample with respect to the specimen and other anatomy. Staining is applied to the sections. Typically, the glass slides are immersed or otherwise exposed to a defined stain to make certain characteristics visually appear in a tissue section for a microscopic review.

The WSI of thin tissue sections can be digital images of a glass (or other suitable substrate) slide with a thin section of tissue depicted by a medical microscope. The WSI can be high resolution and have between about $1 \times 10^3$-$1 \times 10^{12}$ pixels, and a magnification typically about 0.1-1.0 micrometers per pixel. Today there are many scanners capable of producing high-quality digital images from microscopy glass slides. See, e.g., Rojo et al., Critical comparison of 31 commercially available slide systems in pathology, Int J Surg. Pathol., 2006; 14(4):285-305, the contents of which are hereby incorporated by reference herein. The resulting WSI digital images can be very large, for instance 30,000×40,000 pixels, 100,000×100,000 pixels or more. In histology, a two-dimensional (2D) image often suffices, but there is also the possibility to produce slices across the depth of the tissue section, creating a three-dimensional (3D) dataset even though the extent in the z-direction can be far different from the x-y directions.

The term "viewer" refers to an electronic interface that allows a user to select to display different images and different magnification levels of target tissue, typically tissue associated with WSI.

The term "virtual cut location marks" refers to electronically generated representations of physical cut mark locations placed on a macroscopic image or model of a grossing specimen to represent actual physical cut locations made on a specimen to acquire tissue samples. The term "virtual color location marks" refers to electronically generated representations of physical color locations placed on a macroscopic image or model of a grossing specimen to represent actual physical locations where color is applied to the grossing specimen associated with acquired tissue samples. The virtual cut location and/or color marks can be provided as electronic objects onto an actual macroscopic image of the specimen or a macroscopic model of the specimen.

The term "macroscopic" refers to a view of the grossing specimen itself (image or model) rather than a microscopic view of thin tissue slices.

Embodiments of the invention recognize that image analysis tools in pathology/cytology can be challenging as they should fit well into the routine clinical workflow. In comparison to a research lab setting, this means additional requirements of precision, robustness and performance (e.g., throughput speed). For instance, waiting a few minutes for an image processing algorithm to finish is unfeasible, whereas that may be considered quite reasonable in a research setting.

Referring to FIG. 1, an exemplary grossing system 100 with a grossing workstation (or "station") 105 is shown. The grossing station 105 includes, for example, a cutting region 106, typically provided with a cutting board or plate 12 and at least one camera C for obtaining one or more images of a grossing specimen G of patients. The at least one camera C is typically a macroscopic camera such as PathStand™ 24 available from Diagnostic Instruments, Inc, Sterling Heights, Mich., USA.

The grossing system 100 can also include a cut mark circuit 30 that is configured to automatically, electronically identify physical cut locations to define a respective physical cut location 10 (10$i$ to 10$n$) associated with a current location of an excision tool 20, such as a scalpel or knife, at time (t) in relation to the grossing specimen G. The circuit 30 can render a visual virtual representation of a respective physical cut location 110$_1$ (e.g., a virtual cut location mark) at a correct spatial location on one or more macroscopic images M of the specimen G which can be shown on a display 35 (during the cutting and/or at a viewer V (FIG. 4), at or downstream of the grossing station) 105.

The circuit 30 can be configured to provide the at least one macroscopic image M with the virtual cut mark representations 110$_1$ to 110$n$ to one or more displays 35. The number "n" typically means between 2-50 and corresponds to the number of physical excisions and associated cut mark representations made on a respective specimen G.

Figure 3:
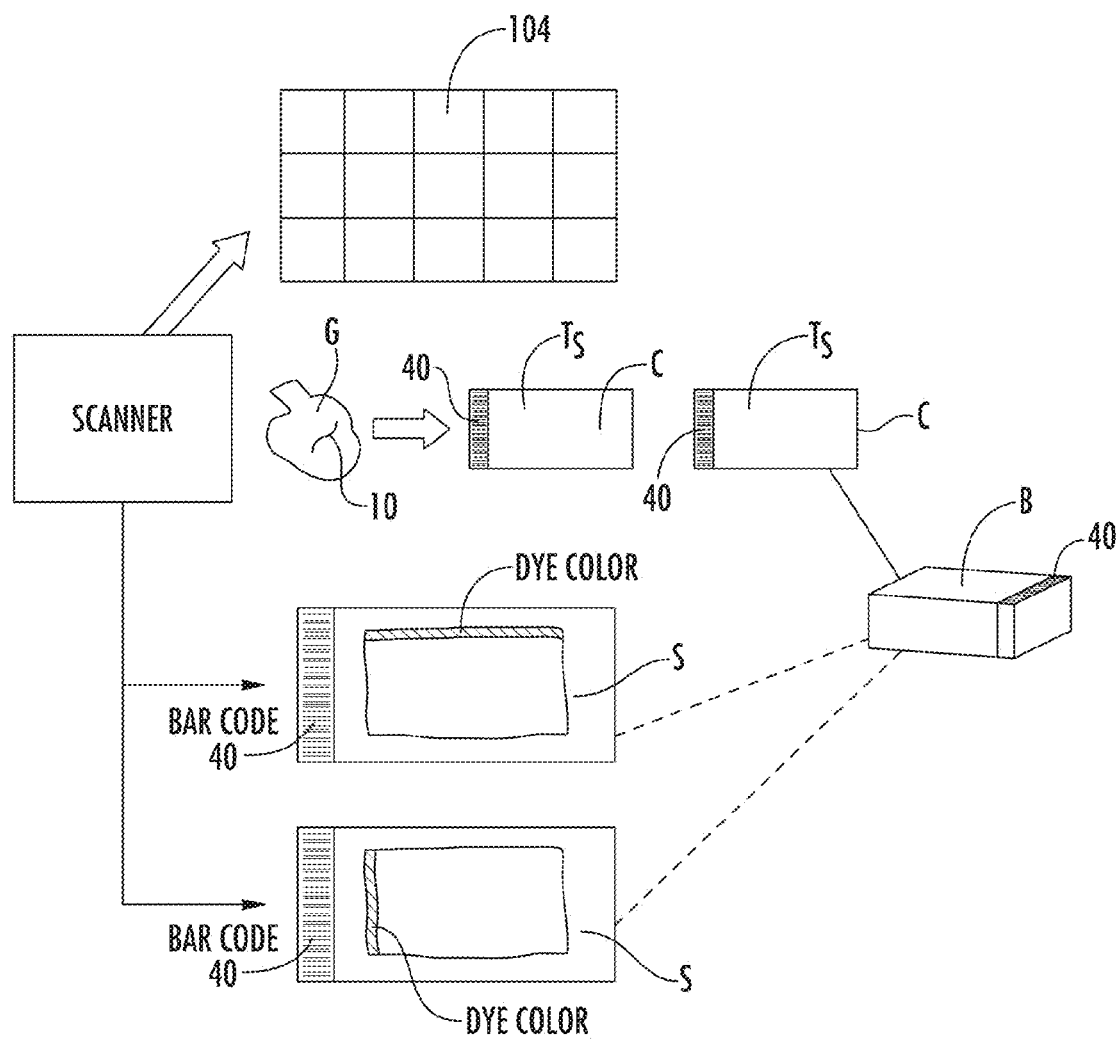
FIG. 3 is a schematic illustration of a grossing system that can digitally correlate cut mark location with slides of tissue samples for a viewer according to embodiments of the present invention.

As shown in FIG. 3, the work flow is carried out carefully to track the specimen G and resultant tissue samples Ts and sections S in the laboratory: The typical situation is that there are barcodes 40 generated/provided or updated at each step. When a tissue sample Ts is cut, it goes into a bar-coded cassette C, which is correlated or registered to being "block X of specimen Y" from cut location "1." When tissue sample section(s) from a block B goes onto a glass slide S, the barcode of the slide S can be correlated and/or registered to being "glass Z of block X." The glass slide barcode 40 can be scanned by the scanner with a respective tissue section on the slide S for a digital microscopy WSI or digitally read by a digital reader or even manually input to correlate and/or register the identifier data during digital scanning via a scanner of respective slides S. The digital WSI image can be identified, correlated and/or registered as "WSI W=glass Z of block X." The specimen G, block B, and slide S to cut location data correlations can be held in a data record file 104 of a database managed by an electronic processing system such as, but not limited to, a type of information system called LIS or LIMS (Laboratory Information [Management] System) as is well known to those of skill in the art. The WSI from the scanner can include dye colors on respective slides S which can be digitally identified (green on right side or end of slide, for example).

The bar code 40 can comprise one or more of a 1-D, 2-D (UPC or Quick Response code or "QR", for example) or even a 3-D bar code. Different types of bar codes can be used for different steps in the work flow. It is also contemplated that the system 100 can be configured to employ other devices/ways of providing the correlation and/or tracking data, such as, for example, RFID tags, magnetic strips or smartcards (such as used with credit cards) with a microprocessor, for example. Associated readers and processing systems can be integrated into the LIS system or grossing synch circuit 100.

The circuit 30 can be configured to correlate virtual cut mark locations 110 on the macroscopic map M (FIG. 4) to the tissue samples Ts taken from the respective cut locations 10 on the specimen G. Thus, for example, different tissue samples from different cut locations can have unique electronic identifiers that correlate a tissue sample Ts with a physical cut location 10 and/or the corresponding virtual cut location 110. This correlation data can be subsequently integrated with block identifier data (paraffin block of the tissue sample). Thus, the circuit 30 can be configured to provide information to a grossing synch system 100 that provides cut location data for a respective slide, including its virtual physical cut location 110 on a macroscopic image M.

In some embodiments, the electronic database record 104 a slide S of a tissue section can include a data stream that identifies a patient, a specimen G, and tissue sample cut locations 10 and/or 110, and a slide section alphanumeric identifier associated with the S (WSI) on a viewer V.

Figure 4:
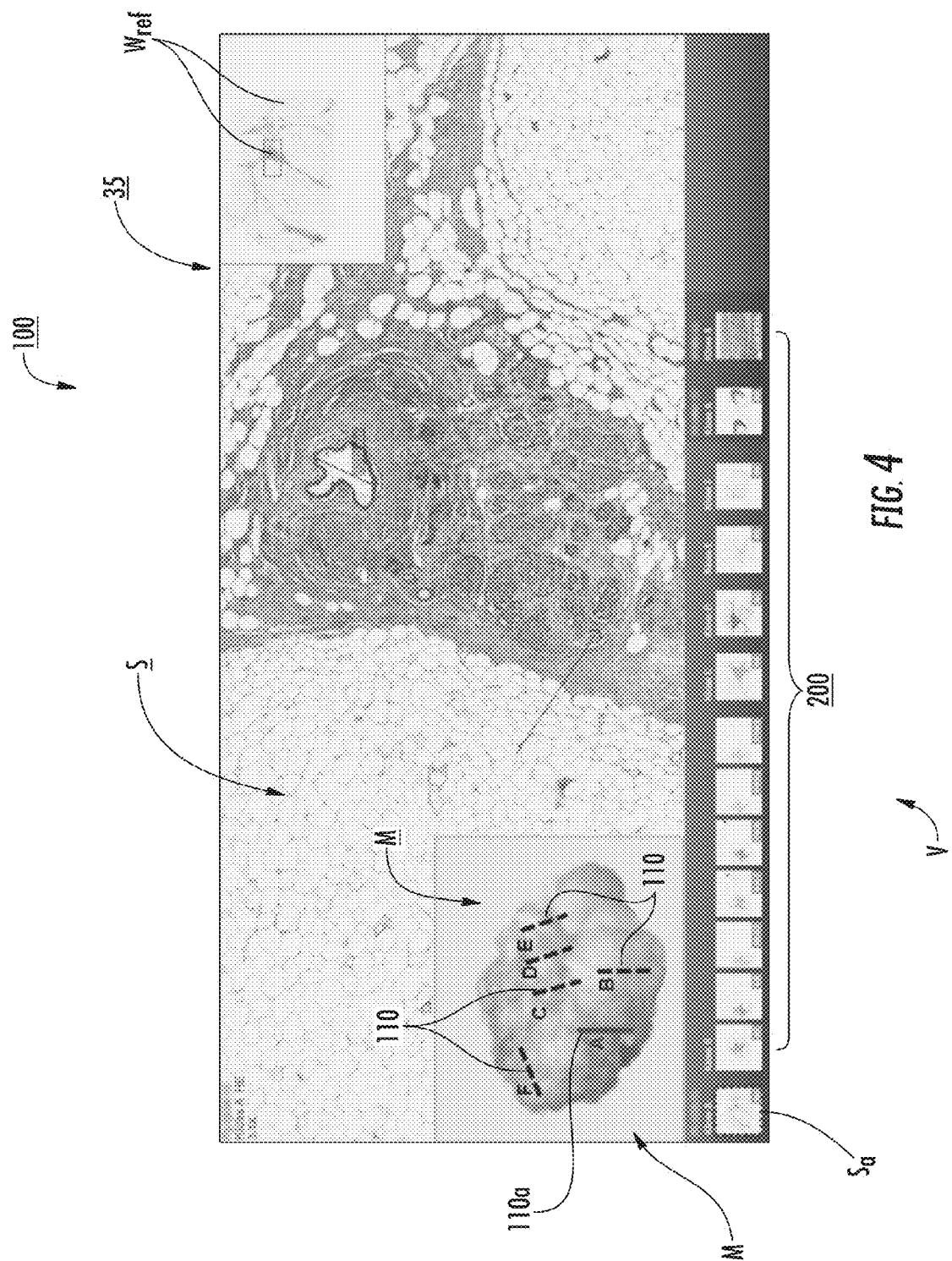
FIG. 4 is a screen shot of a display of an exemplary viewer providing a microscopic image concurrently with a macroscopic image with one or more cut mark locations shown and/or with a current cut location associated with a tissue section of a WSI in a large window or portion of a display according to embodiments of the present invention.

FIG. 4 illustrates an exemplary viewer V with a display 35 that shows a macroscopic image M with the virtual cut marks 110. A WSI view of a slide S is shown with the macroscopic image M in a smaller window adjacent or overlaid on the WSI view of the slide S. The system 100 can be configured to visually indicate which cut location mark 110$a$ is associated with the current WSI slide, e.g., current slide Sa is associated with visually enhanced cut location mark "A." The cut location marks 110 may be represented as linear overlay objects and/or lines with a unique alphanumerical label as shown. The relevant cut location mark 110$a$ associated with the currently viewed slide Sa can be visually enhanced relative to other cut location marks 110, e.g., shown in bold, with increased intensity and/or opacity and/or in a different color from non-relevant cut marks. The viewer V may be configured to show only the relevant cut mark 110$a$ and omit or greatly reduce the intensity and/or visual prominence of the non-relevant cut marks (the cut marks not associated with the current slide Sa on the display 35).

The viewer circuit Vc may be configured to visually enhance a relevant physical cut location (e.g., highlight and/or apply a color or border to the cut location) in a macroscopic image M that corresponds to the slide in the viewer V rather than apply overlays or location identification objects.

The cut location marks 110 on a respective macroscopic image or model M may be configured as active or inactive objects or links. For active objects or links, a user may select (e.g., click or touch) a particular cut location mark 110 on image or model M on the display 35 and the viewer V can automatically present WSI slides S associated with the selected cut location mark. The resulting presentation on the display 35 can be to provide the relevant slides S in a new larger viewing window, in a concurrent adjacent or overlay window and/or along one side of the macroscopic image M. A set of thumbnail WSI images 200 of different slides S may be concurrently displayed along a side, top or bottom of the screen. The slide Sa being currently viewed by the viewer V can be highlighted, shown as color coded perimeter matching a color of the visually enhanced cut 110a (cut A). The set of slides 200 may be displayed via a pull down option, for example, or in subsets of slides, relative to a particular block B or a particular cut location, for example.

A UI 130 (FIG. 13) associated with the viewer V can be configured to allow a user to customize viewing sets or select predefined groups for facilitating faster reviews. For example, all slides from the same cut location, typically some with different stains, may be grouped together, e.g., adjacent each other, shown only in the thumbnail set 200 (with other slides from other cut locations omitted) and/or concurrently shown with all slides but emphasized with a common color background and/or perimeter, with an adjacent icon or with an overlay. In some embodiments, each slide S associated with a respective cut location mark 110 can be color-coded to the mark of that location, e.g., the object overlay line can have a color that is the same as that of the slide background and/or perimeter border, for example. Thus, each mark 110 can be shown with a defined color that corresponds to the slide color indicia, e.g., each mark 110 and its associated slides S can be shown all in green, red, fuchsia, pink, yellow and the like.

Still referring to FIG. 4, the viewer V may optionally also be configured to provide a reference window Wref which shows an overview of the entire currently viewed slide Sa.

There may be more than one macroscopic image M for a specimen G. For example, the specimen G may be turned over for additional tissue samples from different cut locations. The circuit 30 can generate a corresponding number of macroscopic images M to show the associated cut mark locations 110. Also, it is contemplated that, when cutting the specimen G, its shape may change. Thus, in some embodiments, the circuit 30 can be configured to employ image registration to adjust for shape changes and other accidental movement. Thus, for example, a first or base image can be obtained. Then, whenever a cut (and/or dye mark or inking as will be discussed below) is made, a new macroscopic image can be obtained/captured. An image registration module (e.g., software) can identify spatial transformation (warping) of the second or subsequent image that is necessary to fit the base image. That spatial transformation can then be applied to the location of the new virtual cut mark 110, such that it becomes correctly related to the base image M. There are many alternative methods that could be suitable for the macroscopic image registration, for example Bowen, F.; Du, E.; Jianghai Hu, "New region feature descriptor-based image registration method," Systems, Man, and Cybernetics (SMC), 2012 IEEE International Conference, vol., no., pp. 2489, 2494, 14-17 Oct. 2012, the contents of which are hereby incorporated by reference as if recited in full herein.

Different specimens G from the same or different patients may have different numbers of cuts $10i$-$10n$ at different locations between specimens G and/or specimen types; thus, the corresponding virtual cut marks $110_1$-$110n$ can reside at different locations in the macroscopic image M of the specimen G.

At the grossing station 105, when a user wants to make a cut 10 and create an associated virtual or digital cut mark 110 location with a correct physical location for the image M, he/she can initiate a cutting and, concurrently, the circuit 30 can, automatically or based on input from a user interface (UI) associated with the circuit 30, initiate or activate the circuit 30, to generate data to and/or make a corresponding marking 110 for a macroscopic image M, while the user is holding the cutting instrument (e.g., scalpel) 20 at cut location 10 on the specimen G. Thus, the circuit 30 can be in communication with at least one camera C at the workstation 105 to obtain at least one macroscopic image concurrent with a physical cut of the specimen for a respective tissue sample.

The circuit 30 can generate a virtual mark 110 of a respective cut in real time or near real time, e.g., while a corresponding physical cutting is carried out, typically within 0.001 second to about 1 second of actual initiation of a respective cutting or upon contact of a cutting instrument 20 to the specimen G. However, in embodiments, the circuit 30 can generate the virtual markings 110 later, e.g., after the specimen G leaves the grossing station 105, based on data collected during the grossing procedure of the specimen G.

In some embodiments, no separate marking tool is required for the virtual marking. For example, a cutting instrument 20 (e.g., scalpel) used for the specimen cutting can also be configured to generate the virtual mark 110. In some embodiments, the cutting instrument 20 can include a circuit interface $20i$. For example, the cutting instrument 20 can comprise a user interface UI that communicates with the circuit 30. The UI may be configured as a hand, finger or thumb input. The UI may comprise a pressure sensor. Thus, for example, as a clinician presses on the cutting implement 20 to cut tissue, an increase in pressure or force on the input $20i$ can generate a signal to the circuit 30 that actual cutting is occurring, thus triggering a camera shot and/or marking of a virtual cut location 110 corresponding to the physical cut location 10.

Figure 2A:
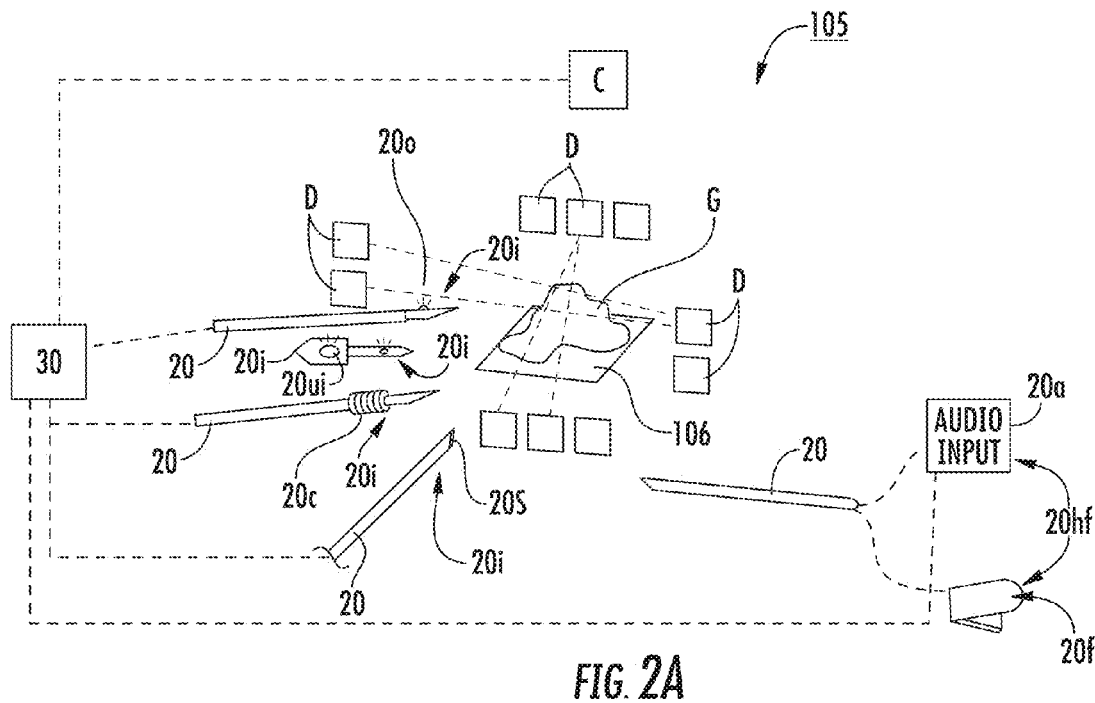
FIGS. 2A and 2B are schematic illustrations of additional exemplary grossing workstations for automatically, electronically obtaining cut mark and/or dye locations during a grossing procedure according to embodiments of the present invention.

Referring to FIG. 2A, in some embodiments, the cutting instrument 20 can have various circuit interface configurations for communicating when and where to make a virtual mark 110. For example, the cutting instrument 20 can comprise a sensor $20s$ on a bottom tissue contacting end portion that contacts tissue to complete a circuit, close a switch or detect force or pressure upon contact/cutting action. In some embodiments, the interface $20i$ can comprise a UI $20ui$ which can be positioned as a finger or thumb position that allows an easy-to-use interface that can be carried out in response to when a user initiates a cutting force with a finger or thumb. In some embodiments, the cutting instrument 20 can include at least one fiducial or optical signal feature $20o$ that can be interrogated in a workstation 105 (in a defined volumetric space) and/or in image data to identify when a cut is occurring and/or a cut mark location. In some embodiments, to initiate the virtual marking 110, the circuit 30 can be configured to respond to a hands-free command signal $20hf$, for instance by pressing a foot pedal 20f or using a voice-activated command (audio input) 20a. Combinations of the different circuit interfaces 20i may be used.

In some embodiments, a separate marking tool may be used to mark the cut location on the specimen after tissue sample is excised. Thus, the tool may be configured as a pen-like device that traces over a cut on the specimen G to generate the virtual cut marking location 110.

FIG. 2A also illustrates that a grossing workstation 105 can comprise optical detectors D that may be used with one or more cameras C to determine when a cutting instrument 20 is in or approaching the specimen volume G to obtain an image and/or generate the cut mark location 110. The detectors D may be optical, e.g., infrared sensors, for example, with transmitters/emitters and receivers positioned across the specimen G.

Figure 2B:
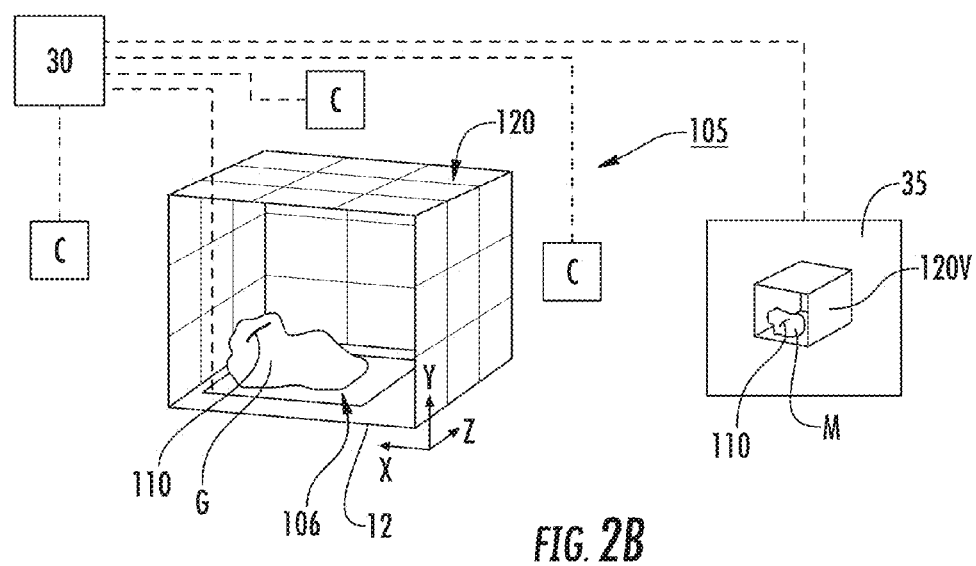

FIG. 2B illustrates a grossing workstation 105 with a grid 120 forming graduated, incremental markings for a volumetric, Cartesian, coordinate system. The grid 120 can be used to define coordinates of respective cut marks in the workspace at the workstation 105 that can be electronically converted to the virtual markings 110. The cutting board or plate 106 may optionally be used to provide X and Y axis markings in the plane of the board or plate 106. A macroscopic image M can be generated with a virtual box-like grid 120v in the virtual space to identify the cut marks 110 on the display 35. The grid 120 may be faded or turned on and off on the display via the system 100 such as the location marking circuit 30 or another module via a Ill.

The tracking of the cutting instrument 20 and/or identification or orientation and length of a particular cut mark can be carried out in several ways. One possibility is to use image analysis techniques. For example, a first pre-cut (base) image of the specimen G can be captured. Referring again to FIG. 1, the top of the cutting tool 20u can comprise a visually recognizable or enhanced (e.g., conspicuous) color, LED or other optical feature and/or a defined shape that can be identified by image recognition, for example. When a cut 10 is made on the specimen G, another image can be captured. An image analysis circuit/module (e.g., software) can be used to identify the location of the scalpel top 20u and create a digital virtual cut location mark such as a "cut reference object" referring to a location in the base image. The "cut reference object" can be shown as a marker on the base or pre-cut image (which can be registered to a subsequent macroscopic image M or can be the macroscopic image or model M for the viewer).

Other tracking possibilities involve other ways of locating a cutting instrument (e.g., scalpel blade), such as using infrared or magnetic tracking devices, e.g., tracking coils opto-electronic transmitters, transponders, GPS tracking and the like.

The circuit 30 can be configured to identify a location in 3-D space with a coordinate system or with relative measurements of location to generate the virtual cut mark representations 110 with a proper orientation, length, width and position on the macroscopic image M corresponding to a respective physical cut on the specimen G.

Figure 5:
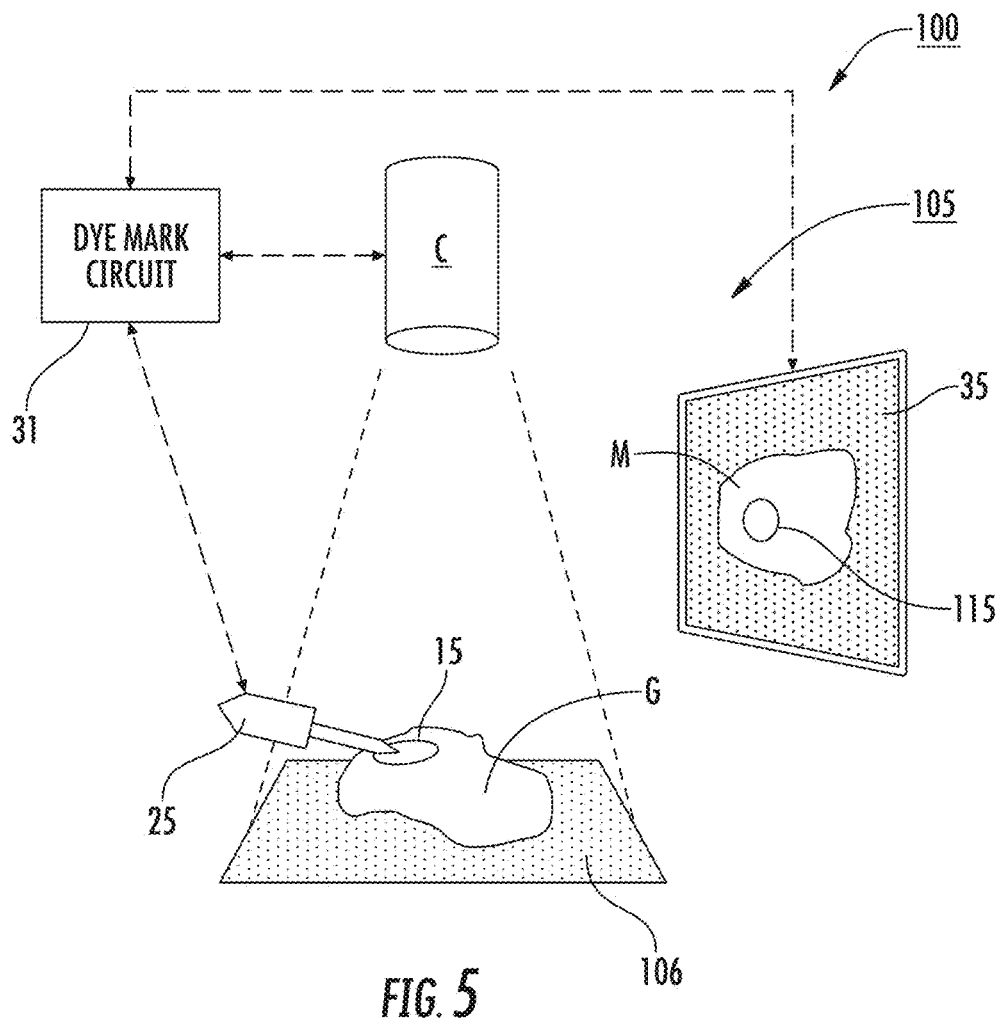
FIG. 5 is a schematic illustration of a grossing workstation that can provide electronic data of dye mark locations on a grossing specimen image for display on a macroscopic image or to be able to correlate viewer user views of WSI microscopic slides according to embodiments of the present invention.

Referring to FIG. 5, in some embodiments, the grossing sync system 100 can alternatively or additionally be configured to convert a region of the specimen G marked with color into a digital object with reference to a location of the macroscopic image M. When color is applied via an applicator 25 to an area or volume 15 of the specimen G (a.k.a. inking), a user and/or a dye mark circuit 31 initiates creation of a digital "dye" or "color" reference object 115 (which can also be described as a "virtual color location maker").

The grossing system 100 may be configured to correlate a slide S to an applied color mark. The colors (e.g., dyes) are typically not involved in keeping track of blocks B (FIG. 3) or tissue samples on slides S (FIG. 3). However, the color (e.g., dye) is typically visible both at a macroscopic level and in the sections viewed in the microscope. Thus, where the color is associated with a dye, the dye is visually apparent in a WSI image viewed on a display or screen. The color helps a reviewer, e.g., a pathologist, when looking in the microscope/WSI viewer to relate the orientation to the macroscopic situation. The pathologist or other reviewer looks to the section, the dye color and a macroscopic image to assess how the WSI view of a section S on display relates to the specimen, e.g., "Is this side facing towards organ X?" To relate the slide to the orientation, the color dye can provide the information, e.g., ". . . it has blue dye and now that I look at the counterpart macroscopic image I can see blue dye at this location which identifies which side of the specimen G it corresponds to."

The macroscopic location associated with an applied color can be conveyed through a macroscopic image or photograph of the specimen. Conventionally, the location is perhaps more commonly just denoted as text in a macroscopic sketch of the specimen drawn by hand at grossing. The dye color/side correlation may be based on standardized dye marking routines, e.g., one side of this type of specimen is always dyed green. Thus, while the color is typically applied via dyes, inks or other color substances may be used whether in liquid, powder, gel, spray or other formulation.

The system 100 and/or circuit 31 can be configured in several different manners to carry out the dye color representation on the macroscopic image M by electronically identifying the location of the inked area(s) 15. As for the cutting instrument 20 discussed above, the color (e.g., dye) applicator 25 itself can be used along the lines of any of the techniques and features discussed above. For example, the dye area can be identified through a defined visually enhanced (contrasting or conspicuous) color and/or a defined shape of the dye applicator tip, by magnetic or infrared tracking at the workstation 105. The dye identification can be configured to electronically, automatically distinguish between different colors. As for the above, instead of or with tracking configurations, image analysis and/or image recognition protocols can be used. Thus, for example, an image of the specimen G can be obtained concurrently with the dye application and through image analysis the system can identify an inked area and which color that has been used.

The initiation of the virtual dye marking 120V can be performed similarly to the cut location. In some embodiments, the initiation can be done automatically without manual initiation. For example, the system 100 or circuit 31 can be configured to continuously capture images over a grossing procedure and/or over a portion of a grossing procedure (such as when a dye applicator approaches the specimen similar to the cutting instrument discussed in FIGS. 2A and 2B, for example). When a color (e.g., dye) applicator 25 is identified while a new color appears on the specimen G, a virtual color location mark 115 can be made. In some embodiments, the applicator 25 can be configured to change appearance in a visually detectable manner when color (e.g., dye) is released, which can be identified through image analysis. In some embodiments, the applicator 25 can transmit a signal when dispensing dye.

Figure 6:
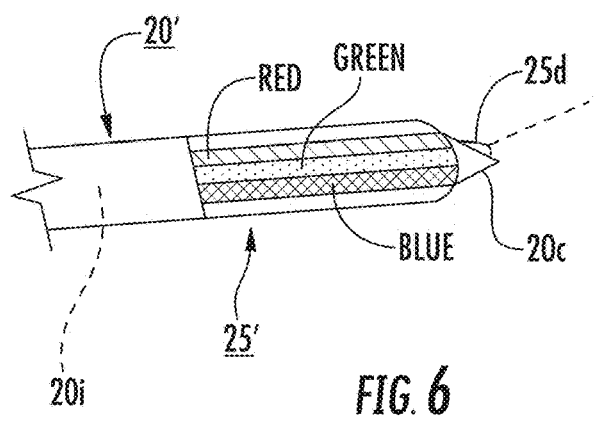
FIG. 6 is a partial schematic illustration of a combined cutting instrument and dye marking applicator according to embodiments of the present invention.

FIG. 6 illustrates that a hybrid cutting instrument 20' with a cutting surface 20 which includes an onboard color applicator 25' with a dispenser 25d positioned proximate the cutting surface 20c. Thus, the instrument 20' can be used to both cut tissue samples 10 and dispense color 25d, either serially or concurrently. The applicator 25' can be configured as a rotatable cartridge of different colors that can be automatically incremented with different cuts or may be user selected with a user input similar to a color-selectable ink pen or marker. The hybrid instrument 20' can be configured with a circuit interface 20i to generate the cut marks 110 and the color marks 115 on a macroscopic image or model M.

Figure 7:
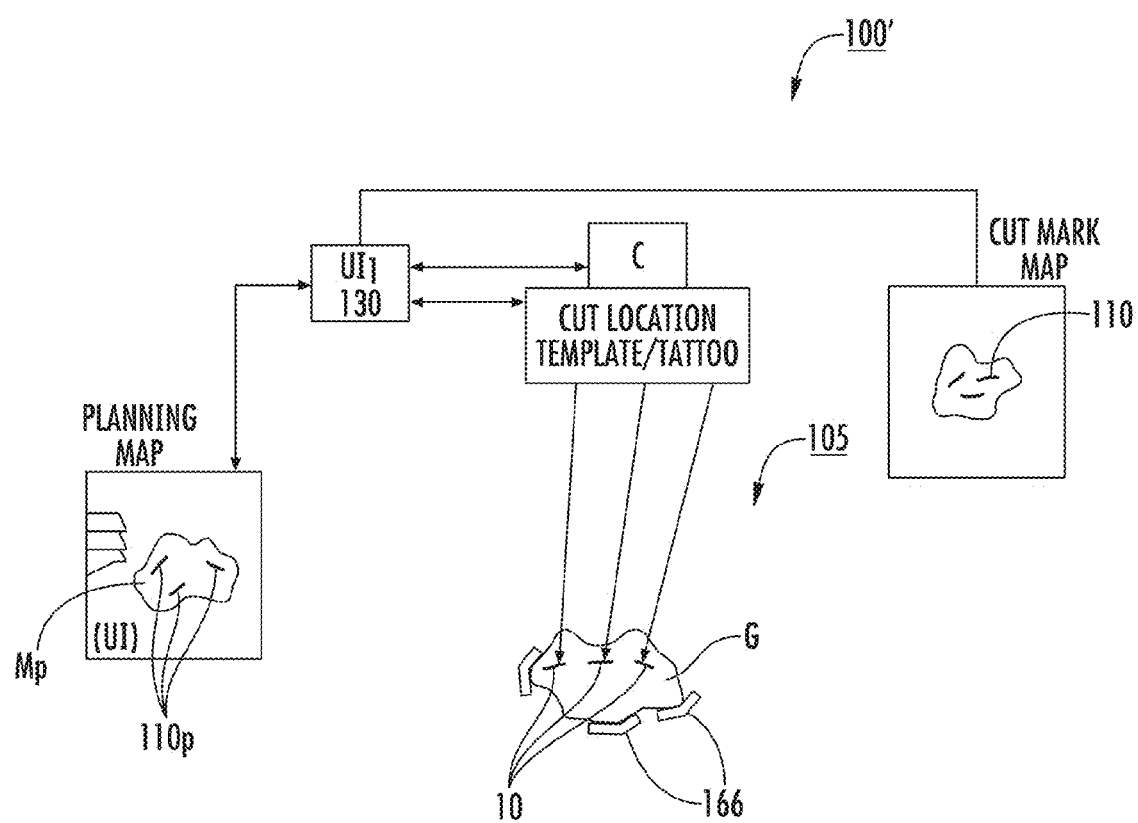
FIG. 7 is a schematic illustration of yet another embodiment of a grossing station for identifying cut mark and/or dye locations on a specimen and generating virtual marks on a macroscopic image and/or correlating microscopic views to facilitate user comprehension of microscopic tissue sections to the grossing specimen according to embodiments of the present invention.

FIG. 7 illustrates an exemplary grossing workstation 105 configured with a different workflow protocol for identifying cut locations 110 and/or dye marks 115 (although discussed with respect to the cut locations). As shown, a planning image or map Mp of the grossing specimen G can be provided on a display. A user can select desired cut locations for tissue samples. The grossing system 100' can generate a template of defined cut locations onto the specimen G based on the defined cut marks 110p on the planning image or map Mp. The system 100' can be configured to provide a light template that projects a tattoo type line or lines over the specimen G at defined cut locations. In some embodiments, the system 100' can be configured to generate a color-based (printed or sprayed) tattoo which can be automatically applied with different dye colors which may be defined by standard routines for different cut orientations at different cut locations. Image registration can be used after each cut is made or after all cuts are made to match an actual cut with a virtual cut mark 110 based on the planning cuts 110p as a starting point for the macroscopic image M. A set of releasably attachable anchors 166 can be used to hold the specimen in position on the board or tray, for example.

Figure 8:
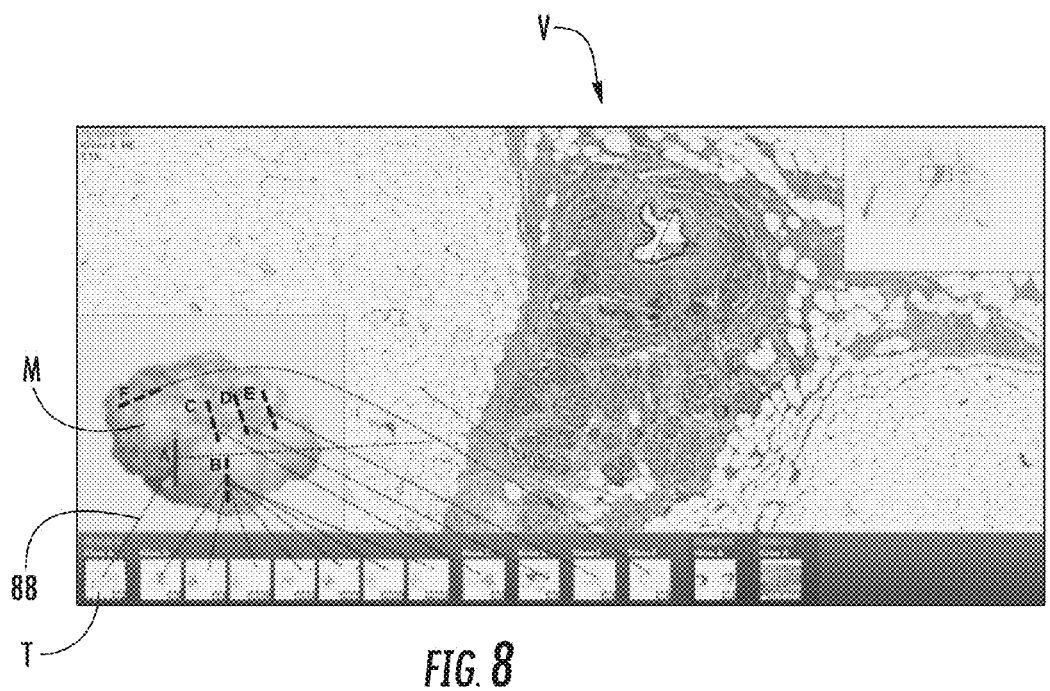
FIGS. 8-10 are screen shots of examples of viewer display windows with correlated microscopy images for histology analysis according to embodiments of the present invention.
Figure 9:
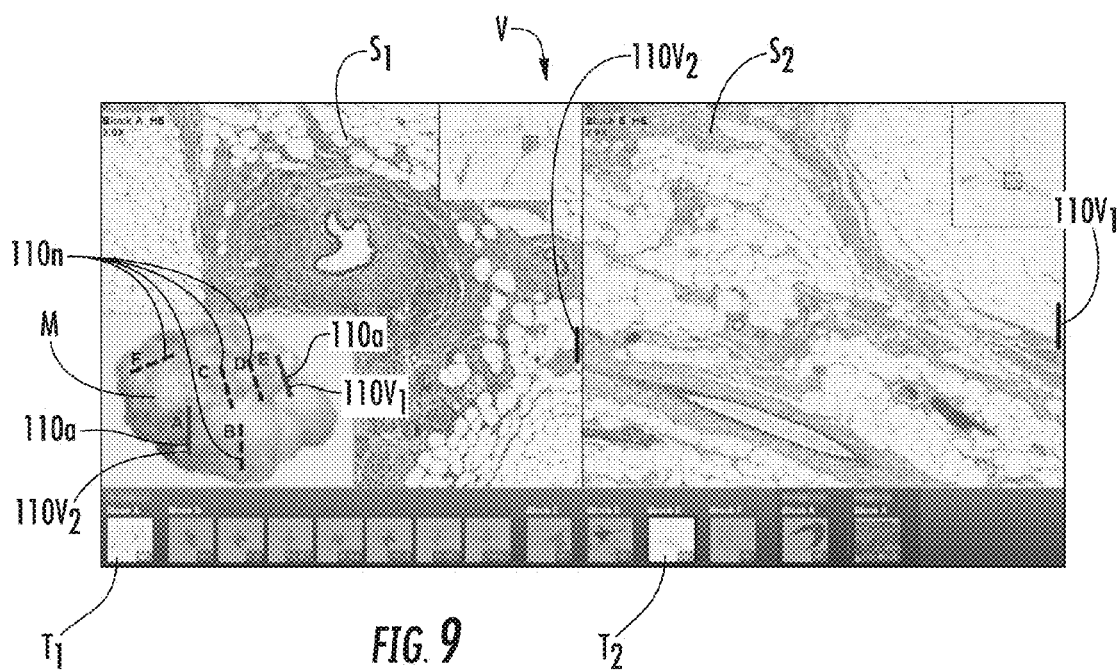
Figure 10:
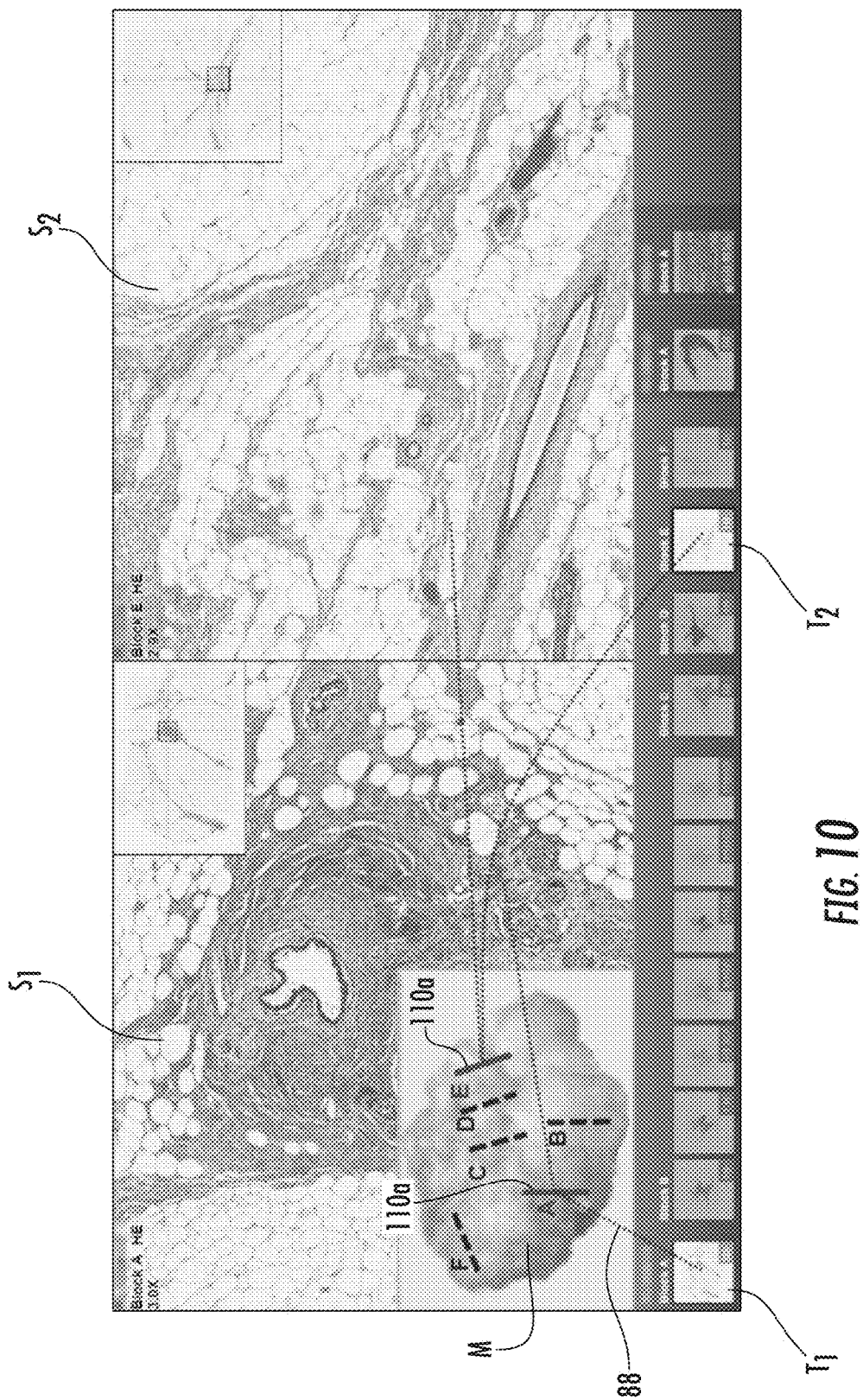

As discussed above with respect to FIG. 4, and as shown, for example in FIGS. 8-10, the viewer V can be configured to provide one or more macroscopic images M that can include virtual cut location marks 110 that can be viewed in connection with the slide images S.

The virtual cut location marks 110 can be provided as "cut reference objects" shown as overlays on the macroscopic image(s) M. These virtual cut location marks 110 can be electronically connected to the corresponding slides S. Typically, the electronic connection can be shown in a visually distinct manner for easy intuitive visual recognition by a user. Thus, for example, the viewer V can electronically designate to a user which cut mark is associated with the slide under review.

In some embodiments, a set of slides S of a specimen G can be provided in one or more adjacent windows to a larger view of a tissue section of a slide S under review, typically along a perimeter of the larger WSI view on the display.

Some or all of the slides S of a particular specimen G can be provided as thumbnail images in a GUI, which may include a touch screen GUI or other GUI input. The visual connections can be in the form of highlighting the virtual mark location 110a (e.g., cut overlay) corresponding to the slide being viewed Sa and/or dimming the other virtual cut marks 110.

Where there are thumbnail image overviews of the slides 200, a corresponding thumbnail T of the slide Sa can be visually changed in a defined manner relative to non-relevant slides to intuitively relay to a user which slide is under review and from which cut location the tissue section on the slide was obtained. The visual change can be a visual enhancement (FIG. 8), e.g., visually enhanced to have a different color or intensity or brightness relative to other slides in the thumbnails and/or the other slides may be visually dimmed or faded (FIGS. 9, 10) and a respective associated cut mark location can be also visually enhanced (FIGS. 8, 9 and 10). The defined visual change can be via a moving border, use of an icon or arrow or at the thumbnail of the active slide, a hovering mouse pointer or other defined visually distinctive change feature.

FIGS. 8 and 10 illustrate an optional use of tether lines 88 that connect a cut location 110 on the macroscopic image M to a thumbnail slide image T and/or the larger displayed slide sample S. The visual tethers may be faded, dimmed or selected via a UI by a user. Typically, the tethers 88 are not required and may be used via a selection by a user or may be omitted as an option from the viewer V. Where used, the tethers may be just visual tethers or may be active links that allow for more information to be provided to a user for a particular cut location and/or slide.

FIGS. 9 and 10 illustrate that a viewer V can show two large views of slides $S_1$, $S_2$ in high magnification and the corresponding cut location marks 110a ("A" and "E") can be visually enhanced relative to the other cut mark locations. The cut location marks 110a that are related to the current large slide views $S_1$, $S_2$ can be shown as bold, with increased intensity and/or in solid line and/or with a different color relative to the other cut location marks 110 which can also be shown in broken lines. Here, each relevant cut mark location 110a is shown in a brighter, increased intensity and in a different solid line color on the image M.

In some embodiments, as shown in FIG. 9, the two different relevant cut mark locations 110a (here "A", and "E") may be shown in different manners, yet visually enhanced configurations from the non-relevant cut location marks 110n, e.g., each may be shown with a different color $110v_1$, $110v_2$, color-coded to the tissue slide thumbnail $T_1$, $T_2$ (Block A, Block E, respectively) and optionally with visual color indicia $110v_1$, $110v_2$ provided on or adjacent the high magnification larger view of $S_1$, $S_2$ for ease in intuitive visual association.

The virtual color location marks 115 (FIG. 5) can optionally be provided as digital "color reference objects" and may be shown as overlays on the macroscopic image(s). The virtual color marks 115 can be shown as GUI markers in the image views.

Furthermore, the grossing sync system 100 and/or viewer V can be configured to automatically rotate a WSI image S such that a defined applied (e.g., dye) color is presented in a defined orientation by default. This removes the need for manual orientation either at slide preparation or at slide review, or, where orientation is not standardized, can offer a more consistent slide visualization that relieves cognitive load from the pathologist. The viewer V (e.g., a viewer circuit or module) can be configured to rotate a scanned WSI microscopic image according to dye color and present the WSI in a window in a defined orientation, thereby providing a consistent slide orientation view based on location of a defined applied color in a scanned WSI.

Figure 11:
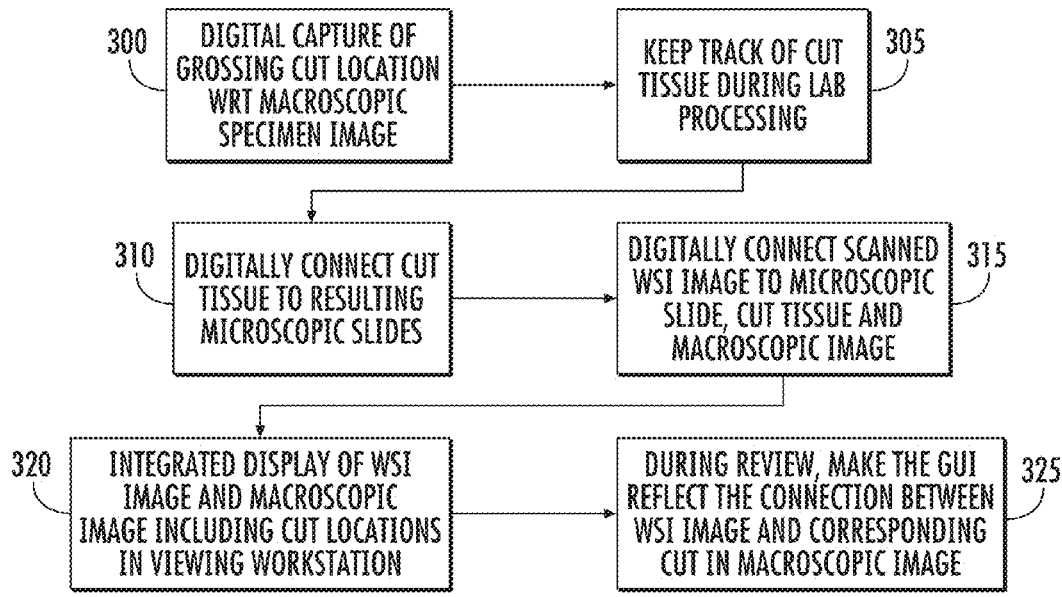
FIG. 11 is a flow chart of an exemplary workflow process to digitally provide cut mark location data for correlating microscopic slide views to physical cut locations according to embodiments of the present invention.

FIG. 11 is a flow chart of exemplary steps that can be used to provide the integrated display of WSI slide images with a macroscopic image that includes cut location marks 110. As shown, grossing cut locations of a physical specimen G can be digitally captured with respect to a macroscopic specimen image (block 300). Cut tissue is tracked during laboratory processing (block 305). Cut tissue is digitally connected to resulting microscopic slides (block 310). Concurrently at least one WSI image and at least one macroscopic image are provided with cut locations on a display associated with a viewer (block 320). The viewer visually connects the WSI image and a corresponding cut location in the macroscopic image (block 325).

Figure 12:
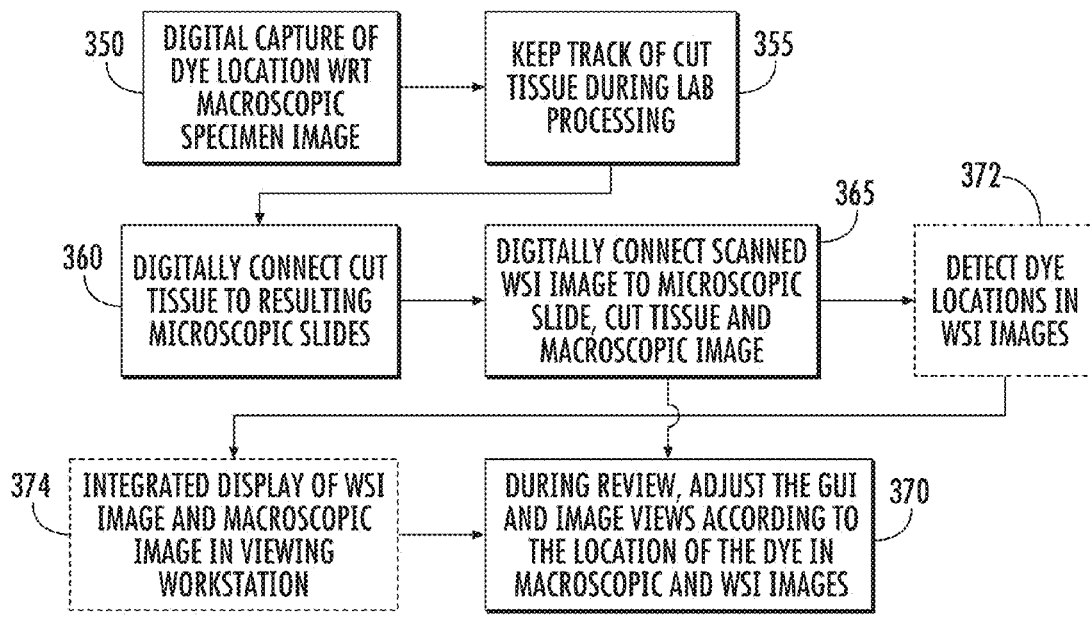
FIG. 12 is a flow chart of an exemplary workflow process to digitally provide dye location on a specimen to digitally correlate microscopic slide views according to embodiments of the present invention.

FIG. 12 illustrates an exemplary workflow of making and using color, e.g., dye, information of a specimen G from a grossing station. Dye locations can be digitally captured with respect to a macroscopic specimen image (block 350). The cut tissue from the specimen is tracked during laboratory processing (block 355). Cut tissue is digitally connected to resulting microscopic slides (block 360). Scanned WSI images are digitally connected to cut tissue and a respective macroscopic image of the specimen (block 365). WSI image views are electronically adjusted according to location of the dye in the macroscopic and/or microscopic images and the adjusted views are provided to a display (block 370). Optionally, before or during the adjusting, dye locations are detected in respective (scanned) WSI images (block 372) and the adjusted WSI image and macroscopic image are integrated into a viewer V for concurrent viewing in a display (e.g., at a workstation)(block 374).

Figure 13:
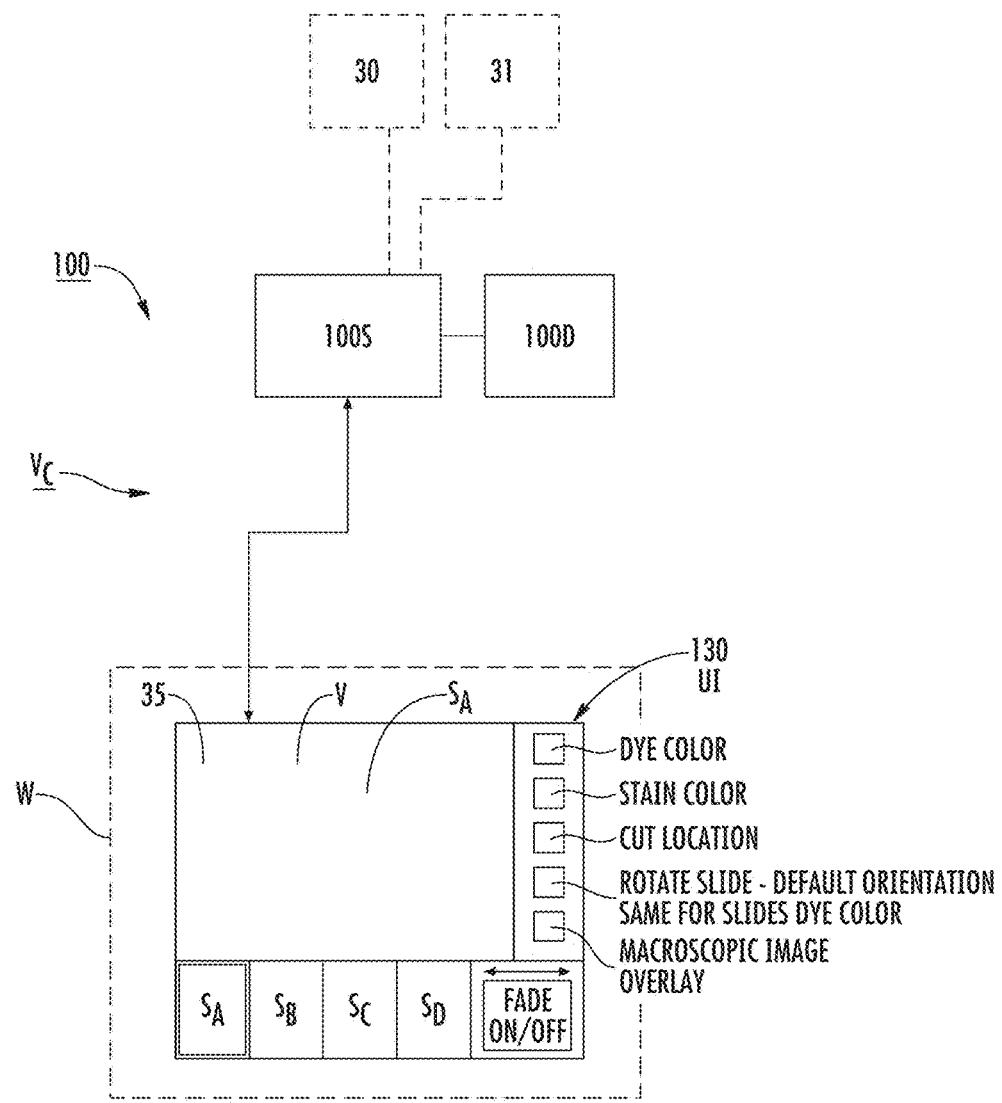
FIG. 13 is a schematic illustration of a viewer with user interface selections optionally in communication with a server and optional medical and/or laboratory record database according to embodiments of the present invention.
Figure 14:
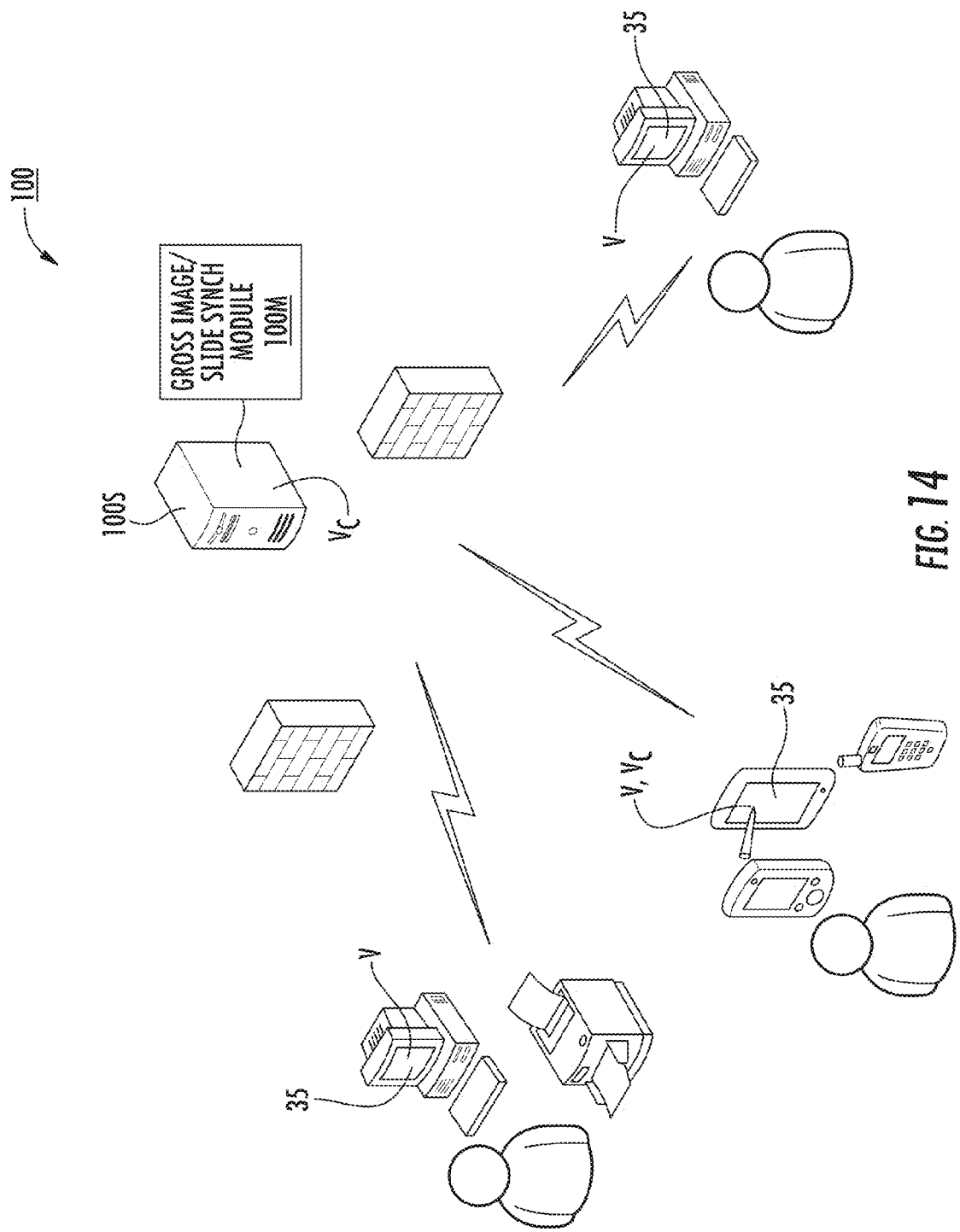
FIG. 14 is a schematic illustration of a circuit comprising a server according to embodiments of the present invention.

FIGS. 13 and 14 are schematic illustrations of a viewer V in communication with a viewer circuit Vc that can communicate with at least one server 100S and at least one database 100D. The viewer circuit Vc may be part of or communicate with the grossing sync system 100 which can include one or both of the cut mark location circuit 30 and the dye mark location circuit 31. The viewer Vc can have a client-server configuration allowing various users to log into a portal hosted by a server to operate the viewer V. The server 100S can communicate with an LIS system that may include some or all of the grossing specimen tracking data or records 104 (FIG. 3), for example.

Referring to FIG. 13, the viewer V can comprise a UI 130 that allows a user to select various WSI presentations. As shown, viewing options can include dye color, stain color, cut location, rotate slide view according to a selected or defined dye color, and a macroscopic image overlay with cut marks (on, off, fade, etc.).

As shown in FIGS. 13 and 14, the viewer circuit Vc can reside at least in part on a server 100S that can be remote from a review/user site. Alternatively, the server 100S can be onsite or the viewer circuit Vc can partially or totally reside onboard a computer associated with a clinician workstation. The server 100S can be integrated into a single server or may be distributed into one or more servers or other circuits or databases at a single physical site or at spatially separate locations. Similarly, the viewer circuit Vc held by the one or more servers 100S, and can be distributed into multiple processors or databases or integrated into one.

The viewer circuit Vc and/or server 100S may be embodied as a standalone server or may be contained as part of other computing infrastructures. The viewer circuit Vc and/or server 100S may be embodied as one or more enterprise, application, personal, pervasive and/or embedded computer systems that may be standalone or interconnected by a public and/or private, real and/or virtual, wired and/or wireless network including the Internet, and may include various types of tangible, non-transitory computer-readable media. The viewer circuit Vc and/or server 100S may also communicate with the network via wired or wireless connections, and may include various types of tangible, non-transitory computer-readable media.

The viewer circuit Vc and/or server 100S can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers.

Users can communicate with the viewer circuit Vc and/or server 100S via a computer network, such as one or more of local area networks (LAN), wide area networks (WAN) and can include a private intranet and/or the public Internet (also known as the World Wide Web or "the web" or "the Internet." The viewer circuit Vc and/or server 100S can comprise appropriate firewalls (FIG. 14) for HIPPA or other regulatory compliance.

FIG. 13 illustrates that viewer V can be in communication with (or onboard) at least one workstation W with a display or screen 35. The display 35 can include a UI 130 which can include touch, mouse, speech, cursor or other inputs that allows a user to select the viewing options.

The viewer circuit Vc or grossing sync system 100 can also include one or more report output devices, including a display 35 (onboard the workstation W or associated with another computer), a printer, a facsimile machine, and pervasive computer devices such as electronic notepads, smartphones, cell phones and the like. A diagnosis based on the analyzed sample can be delivered by email, facsimile, and/or directly to a HIS (Hospital Information System), LIMS (Laboratory Information Management System), PACS systems, or other systems of addresses (electronic or physical).

It is noted that while embodiments of the present invention use a remote server for the image enhancement, it is contemplated that different clinic sites or each facility or room may have a dedicated on site viewer with an image enhancement analysis circuit.

Embodiments of the present invention may take the form of an entirely software embodiment or an embodiment combining software and hardware aspects, all generally referred to herein as a "circuit" or "module." Furthermore, the present invention may take the form of a computer program product on a (non-transient) computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages.

Some modules or routines may be written in assembly language or even micro-code to enhance performance and/or memory usage. However, embodiments are not limited to a particular programming language. As noted above, the functionality of any or all of the program modules may also be implemented using discrete hardware components, one or more application specific integrated circuits (ASICs), or a programmed digital signal processor or microcontroller. The program code may execute entirely on one (e.g., a workstation computer), partly on one computer, as a standalone software package, partly on the workstation's computer or Scanner's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Figure 15:
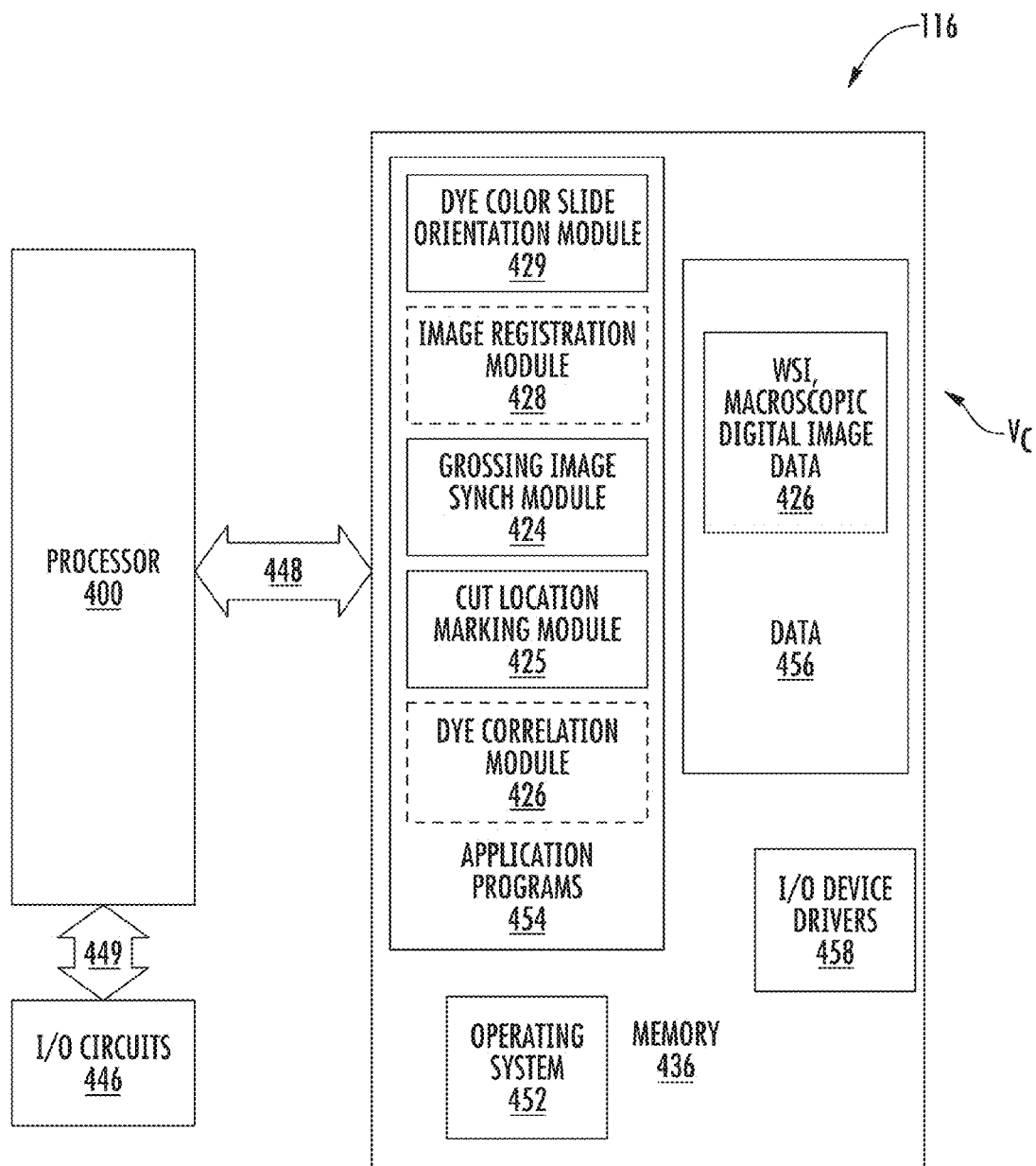
FIG. 15 is a schematic illustration of an exemplary data processing system according to embodiments of the present invention.

As illustrated in FIG. 15, embodiments of the invention may be configured as a data processing system 116 that is in communication with or forms part of the viewer circuit Vc. The data processing system can include at least one processor 400, memory 436 and input/output circuits 446. The data processing system may be incorporated in, for example, one or more of a personal computer, database, workstation W, server, router or the like. The system 416 can reside on one machine or be distributed over a plurality of machines. The processor 400 communicates with the memory 436 via an address/data bus 448 and communicates with the input/output circuits 446 via an address/data bus 449. The input/output circuits 446 can be used to transfer information between the memory (memory and/or storage media) 436 and another computer system or a network using, for example, an Internet protocol (IP) connection. These components may be conventional components such as those used in many conventional data processing systems, which may be configured to operate as described herein.

In particular, the processor 400 can be commercially available or custom microprocessor, microcontroller, digital signal processor or the like. The memory 436 may include any memory devices and/or storage media containing the software and data used to implement the functionality circuits or modules used in accordance with embodiments of the present invention. The memory 436 can include, but is not limited to, the following types of devices: ROM, PROM, EPROM, EEPROM, flash memory, SRAM, DRAM and magnetic disk. In some embodiments of the present invention, the memory 436 may be a content addressable memory (CAM).

As further illustrated in FIG. 15, the memory (and/or storage media) 436 may include several categories of software and data used in the data processing system: an operating system 452; application programs 454; input/output device drivers 458; and data 456. As will be appreciated by those of skill in the art, the operating system 452 may be any operating system suitable for use with a data processing system, such as IBM®, OS/2®, AIX® or zOS® operating systems or Microsoft® Windows® 95, Windows 98, Windows 2000 or WindowsXP operating systems, Unix or Linux™, IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 458 typically include software routines accessed through the operating system 452 by the application programs 454 to communicate with devices such as the input/output circuits 446 and certain memory 436 components. The application programs 454 are illustrative of the programs that implement the various features of the circuits and modules according to some embodiments of the present invention. Finally, the data 456 represents the static and dynamic data used by the application programs 454 the operating system 452 the input/output device drivers 458 and other software programs that may reside in the memory 436.

The data 456 may include (archived or stored) digital WSI and/or macroscopic image data sets 426 correlated to respective patients. As further illustrated in FIG. 15, according to some embodiments of the present invention, the application programs 454 include a grossing image synch Module 424 that can provide virtual cut location marks associated with tissue taken from cut locations on a grossing specimen G. The application programs can include a cut location marking Module 425. The application programs can optionally include a dye correlation Module 426 for correlating dye color to locations on a specimen. The application programs can optionally include an image registration module 428 that can adjust cut mark locations due to specimen shape change. The application programs can optionally include a dye color slide orientation Module 429 for a viewer. The data interface module can be decoupled or isolated from the visualization/viewer module. The application program 454 may be located in a local server (or processor) and/or database or a remote server (or processor) and/or database, or combinations of local and remote databases and/or servers.

While the present invention is illustrated with reference to the application programs 454, and Modules 424, 425, 426, 428 and 429 in FIG. 15, as will be appreciated by those of skill in the art, other configurations fall within the scope of the present invention. For example, rather than being application programs 454 these circuits and modules may also be incorporated into the operating system 152 or other such logical division of the data processing system. Furthermore, while the application programs 424, 425, 426, 428 and 429 are illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 15 but may be provided by other arrangements and/or divisions of functions between data processing systems. For example, although FIG. 15 is illustrated as having various circuits and modules, one or more of these circuits or modules may be combined or separated without departing from the scope of the present invention.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A histopathology and/or cytopathology viewer, comprising:
   a display; and
   a viewer circuit configured to cause the display to concurrently display: (i) a macroscopic view of a grossing specimen with virtual cut location marks associated with orientation and location of actual physical cut locations used to obtain tissue samples from the grossing specimen and (ii) at least one digital microscopic whole-slide image (WSI) of a tissue section from the specimen,
   wherein, for the at least one WSI image on the display, a relevant virtual cut location mark is shown visually enhanced from other virtual cut location marks on the macroscopic view to thereby allow a user to visually connect where the tissue section in the WSI image was obtained during a grossing procedure,
   wherein different tissue samples from different cut locations have unique electronic identifiers that correlate a tissue sample with a physical cut location and/or the corresponding virtual cut location, wherein correlation data is subsequently integrated with block identifier data, and wherein the circuit is configured to access a data record file that provides cut location data for a respective slide, including its virtual cut location on the macroscopic view.

2. The viewer of claim 1, wherein the viewer circuit is configured to visually change a display parameter of at least one of: (a) a relevant virtual cut location mark of the virtual cut location marks on the macroscopic view that is associated with a location on the specimen from which a tissue section of the at least one WSI in the viewer display was obtained; or (b) the virtual cut location marks on the macroscopic view that are not associated with the tissue section of the at least one WSI in the viewer to thereby visually enhance the relevant virtual cut location mark.

3. The viewer of claim 1, further comprising providing thumbnail WSI images of slides associated with the grossing specimen of a patient and visually changing a display parameter of a thumbnail associated with the at least one WSI in the viewer.

4. The viewer of claim 1, wherein a perimeter of the thumbnail or thumbnails associated with the at least one WSI in the viewer display is visually enhanced and/or other thumbnails are dimmed or faded in the display window, wherein the virtual cut location marks are provided as overlay linear objects on the macroscopic view, and wherein a virtual cut location mark on the macroscopic view that is associated with a location on the specimen from which a tissue section of the at least one WSI in the viewer display was obtained is visually highlighted, increased in intensity or changed in color relative to other virtual cut mark locations to thereby visually connect the WSI image in the view to a correct virtual cut location mark.

5. A grossing workstation, comprising:
   a cut mark location identification circuit;
   at least one camera over a workspace at the workstation in communication with the cut mark location identification circuit; and
   a cutting instrument in communication with the cut mark location identification circuit;
   wherein the cut mark location identification circuit is configured to identify physical cut mark locations on a grossing specimen in response to a user-initiated action of cutting the grossing specimen using the cutting instrument and generate corresponding virtual cut location marks on a macroscopic image or model of the specimen for a viewer, and wherein a respective virtual cut location mark corresponds to a physical cut location made by the cutting instrument on the grossing specimen used to obtain a tissue sample such that the virtual cut location marks are given a correct spatial position on the macroscopic image or model of the specimen for the viewer,
   wherein different tissue samples from different cut locations have unique electronic identifiers that correlate a tissue sample with a respective physical cut location and/or the corresponding virtual cut location, wherein correlation data is subsequently integrated with block identifier data, and wherein the circuit is configured to provide information to a grossing synch system of a data record file that provides virtual cut location for a respective slide on the macroscopic image or model.

6. The workstation of claim 5, wherein the cut mark location circuit analyzes a plurality of macroscopic images of the specimen obtained by the at least one camera during a grossing procedure of the specimen, including at least one base macroscopic image obtained prior to a physical cutting to obtain a tissue sample, and wherein the cut mark location identification circuit is configured to electronically place the virtual cut location marks as overlay cut location objects on the macroscopic image or model of the specimen for the viewer.

7. The workstation of claim 5, wherein the cut mark location identification circuit is configured to electronically track movement of the cutting instrument in the workspace.

8. The workstation of claim 5, wherein the cut mark location identification circuit is configured to employ image recognition of movement and location of the cutting instrument in images obtained by the at least one camera to generate the virtual cut mark locations on the macroscopic image or model.

9. The workstation of claim 5, wherein the cutting instrument is configured with a defined leading end portion shape which has a distinct conspicuous visual appearance detectable by image recognition to allow the cut mark location identification circuit to identify movement and contact of the cutting instrument for identifying the placement and orientation of the respective virtual cut location marks.

10. The workstation of claim 5, wherein the cut mark location circuit is configured to employ a hands-free command or input from a user to initiate identifying a cut location.

11. A method of obtaining and/or processing digital pathology and cytology images for viewing, comprising:
electronically identifying when a cutting instrument is approaching and/or on a grossing specimen;
automatically electronically generating virtual cut location marks on a digital macroscopic image or model of a grossing specimen based on the electronic identification, wherein a respective virtual cut location mark corresponds to a physical cut location made by the cutting instrument on the grossing specimen used to obtain a tissue sample such that the virtual cut location is given a correct spatial position on the macroscopic image or model of the specimen;
electronically generating data record files that correlate different tissue samples to different cut locations using unique electronic identifiers that correlate a tissue sample with a physical cut location and/or the corresponding virtual cut location;
electronically integrating block identifier data of the tissue samples into the data record files; and
electronically providing a relevant data record from the data record files to a viewer that provides cut location data for a respective slide, including its virtual cut location on the macroscopic image or model.

12. The method of claim 11, further comprising electronically automatically obtaining a plurality of macroscopic images of the specimen during a grossing procedure of the specimen, including at least one base macroscopic image obtained prior to one or more physical cutting to obtain a tissue sample, and placing the virtual cut location marks on one or more of the obtained macroscopic images or model of the specimen for display in a viewer.

13. The method of claim 11, wherein the electronic identification is carried out by electronically tracking movement of the cutting instrument.

14. The method of claim 12, wherein the electronic identification is carried out using image recognition of movement and location of the cutting instrument in the obtained images.

15. The method of claim 13, wherein the electronic identification of the cutting instrument is carried out using image recognition of a defined leading end portion configuration which is configured as to have a defined distinct conspicuous visual appearance detectable by image recognition.

16. The method of claim 11, wherein the electronic identification is initiated with a hands-free command to a cut location identification circuit in communication with a grossing workstation.

17. The method of claim 11, wherein the electronic identification is initiated by the cutting instrument transmitting a wireless signal at a time of a cut.

18. The method of claim 11, wherein the automatic electronic generation of the virtual cut location marks comprises electronically generating an electronic overlay of at least one cut location object provided as a linear mark and displaying the overlay on a macroscopic digital image or model of the specimen.

19. The method of claim 11, further comprising concurrently displaying (i) a macroscopic image of the specimen with the virtual cut location marks with (ii) at least one digital microscopic whole-slide image (WSI) of tissue from the specimen, wherein a virtual cut location mark associated with the at least one digital WSI is visually enhanced relative to other virtual cut location marks on the macroscopic image when it is associated with where a tissue section from the WSI was obtained from the specimen.

20. The method of claim 19, wherein the virtual cut location marks are shown as respective overlays on the macroscopic image with the visual enhancement provided by highlighting a virtual cut location mark whenever it corresponds to a microscopic WSI image in a viewer.

21. The method of claim 11, further comprising:
electronically automatically obtaining a plurality of macroscopic images of the specimen during a grossing procedure of the specimen, including at least one base macroscopic image obtained prior to any physical cutting to obtain tissue samples, and placing the virtual cut location marks on one or more of the obtained macroscopic images or a model of the specimen for a viewer macroscopic image; and
electronically adjusting for movement of the specimen during a grossing procedure using the base image and one or more of the subsequent plurality of images to register respective virtual cut locations to the viewer macroscopic image or model.

22. The viewer of claim 1, wherein the macroscopic view is shown smaller and adjacent the at least one digital microscopic WSI of the tissue section from the specimen.

23. The viewer of claim 1, wherein the WSI images are generated using scanned slides that are correlated to virtual cut locations and the grossing specimen based on tracked data during laboratory processing.

24. The viewer of claim 1, wherein the virtual cut location marks are straight solid or broken lines applied to an external surface of the macroscopic view of the grossing specimen.

25. The viewer of claim 1, wherein the virtual cut location mark lines can be connected to a corresponding thumbnail image and/or a corresponding location in the macroscopic view of the grossing specimen with electronic tether lines.

26. The workstation of claim 5, further comprising a database in communication with the cut mark identification location circuit that correlates virtual cut location marks shown on macroscopic images of respective grossing specimens with corresponding Whole Slide Images subsequently obtained.

27. The method of claim 19, wherein the virtual cut location mark lines can be connected to a corresponding thumbnail image also shown on the display with the macroscopic image and the at least one WSI of tissue and/or a corresponding location in the macroscopic view of the grossing specimen with electronic tether lines.

28. The method of claim 11, further comprising providing an electronic laboratory database that tissue samples of patients with the virtual cut location marks shown on macroscopic images of respective grossing specimens with corresponding Whole Slide Images subsequently obtained.

29. The method of claim 11, further comprising electronically tracking tissue samples during laboratory processing of blocks and slides of tissue samples using electronically readable bar codes of patient data, virtual cut locations, and slides of tissue samples, and electronically correlating the virtual cut locations of respective grossing specimens to corresponding WSI images based on data tracked during laboratory processing.

* * * * *

UNITED STATES PATENT AND TRADEMARK OFFICE
CERTIFICATE OF CORRECTION

PATENT NO. : 9,984,457 B2
APPLICATION NO. : 14/659229
DATED : May 29, 2018
INVENTOR(S) : Häll et al.

Page 1 of 1

It is certified that error appears in the above-identified patent and that said Letters Patent is hereby corrected as shown below:

In the Specification

Column 13, Line 29: Please correct "I11" to read -- UI --

Signed and Sealed this
Twenty-fifth Day of September, 2018

Andrei Iancu
*Director of the United States Patent and Trademark Office*